(12) United States Patent
Noe et al.

(10) Patent No.: US 10,144,753 B2
(45) Date of Patent: Dec. 4, 2018

(54) ANTHRACYCLINE DERIVATIVES FOR TREATING TUMOR DISEASES

(71) Applicant: Produkem Molekulares Design GmbH, Vienna (AT)

(72) Inventors: Christian R. Noe, Vienna (AT); Michael Sonntagbauer, Vienna (AT); Sébastien Queva, Saint Ouen l Aumone (FR); Ernst Urban, Perchtoldsdorf (AT)

(73) Assignee: Produkem Molekulares Design GMBH, Vienna (AT)

( * ) Notice: Subject to any disclaimer, the term of this patent is extended or adjusted under 35 U.S.C. 154(b) by 62 days.

(21) Appl. No.: 14/435,907

(22) PCT Filed: Oct. 15, 2013

(86) PCT No.: PCT/EP2013/071520
§ 371 (c)(1),
(2) Date: Apr. 15, 2015

(87) PCT Pub. No.: WO2014/060408
PCT Pub. Date: Apr. 24, 2014

(65) Prior Publication Data
US 2015/0252069 A1    Sep. 10, 2015

(30) Foreign Application Priority Data
Oct. 15, 2012 (AT) .................. A 1114/2012

(51) Int. Cl.
| | | |
|---|---|---|
| *C07H 15/244* | (2006.01) | |
| *C07D 265/06* | (2006.01) | |
| *C07D 317/32* | (2006.01) | |
| *C07D 317/34* | (2006.01) | |
| *C07H 15/08* | (2006.01) | |
| *C07H 15/252* | (2006.01) | |
| *C07D 307/20* | (2006.01) | |
| *C07C 15/28* | (2006.01) | |
| *C07C 45/59* | (2006.01) | |
| *C07D 317/26* | (2006.01) | |
| *C07F 7/18* | (2006.01) | |

(52) U.S. Cl.
CPC ........... *C07H 15/244* (2013.01); *C07C 15/28* (2013.01); *C07C 45/59* (2013.01); *C07D 307/20* (2013.01); *C07D 317/26* (2013.01); *C07D 317/32* (2013.01); *C07D 317/34* (2013.01); *C07F 7/1856* (2013.01); *C07H 15/08* (2013.01); *C07H 15/252* (2013.01); *C07C 2603/24* (2017.05); *C07C 2603/44* (2017.05)

(58) Field of Classification Search
CPC ..... C07H 15/08; C07H 15/252; C07H 15/244
USPC ............................................. 514/34; 536/6.4
See application file for complete search history.

(56) References Cited

U.S. PATENT DOCUMENTS 6,355,784 B1    3/2002 Priebe et al.

FOREIGN PATENT DOCUMENTS

| CA | 1131622 | 9/1982 |
| DE | 19708496 A1 | 9/1998 |
| EP | 0523289 A1 | 1/1993 |

OTHER PUBLICATIONS

Arcamone et al, J. Med. Chem. 1976, 19(5), 733-34.*
Arcamone et al, J. Med. Chem., 1976, 19(5), 733-734.*
Fuchs et al, The Journal of Antibiotics, 1979, 32(3), 223-238.*
Christina Sessa et al., "Ongoing Phase I and II Studies of Novel Anthracyclines"; Cardiovascular Toxicol; (2007) pp. 75-79.
C.A. Frederick et al., "Structural Comparison of Anticancer Drug-DNA Complexes: Adriamycin and Daunomycin"; Biochemistry, 29 (1990) pp. 2538-2549.
E.F. Fuchs, et al., New Daunorubicin Analogs "3-Amino-2,3,6-Trideoxy-α and ß-D-Arabino- and 3,6-Diamino-2,3,6-Trideoxy-α-D-Ribo-Hexopyranosides of Daunomycinone"; Journal of Antibiotics, vol. XXXII; No. 3; (1979) pp. 223-238.
T. Matsumoto, et al., "14-Fluoroanthracyclines. Novel Syntheses and Antitumor Activity"; Chemical & Pharmaceutical Bulletin, 36 (10); (1988) pp. 3793-3804.
Y. Kimura, et al., "Novel Glycosidation of 4-Demethoxyanthracyclinones by the Use of Trimethylsilyl Triflate. Syntheses of Optically Active 4-Demethoxydaunorubicin and 4-Demethoxyadriamycin"; Bulletin of the Chemical Society of Japan, 59 (1986) pp. 423-431.
S. Morgenlie, Identification of the Products of Periodate Oxidation of some Mono-O-Isopropylidene Derivatives of Aldoses and Alditols by g.l.c.-m.s, Cabohydrate Research; 138 (1985) pp. 329-334.
N. Cohen, et al., "Synthesis of Optically Active Leukotriene (SRS-A) Intermediates", Tetrahedron Letters, 21 (1980) pp. 4163-4166.
D. Seebach et al., "Self-Regeneration of Stereocenters (SRS)—Applications, Limitations, and Abandonment of a Synthetic Principle"; Angewandte Chemie, International Edition in English 1997, 35, 3708.

(Continued)

Primary Examiner — Ganapathy Krishnan
(74) Attorney, Agent, or Firm — McGlinchey Stafford; R. Andrew Patty, II

(57) ABSTRACT

The invention relates to anthracycline derivative compounds for treating tumor diseases, and related methods, compositions, and kits.

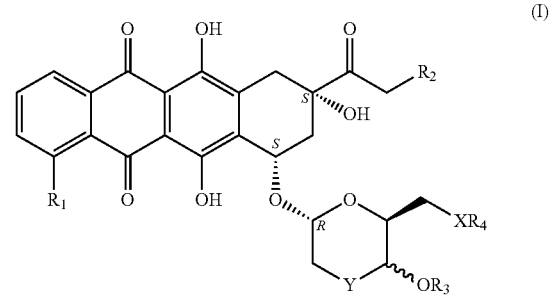

4 Claims, No Drawings

(56) References Cited

OTHER PUBLICATIONS

C. Marschalk, et al., "Marschalk Reaction"; N. Bulletin de la Societe Chimique de France, Mem-oires 1936, 3, 1545; Abstract Only—English Translation; 1 page.
Canadian Office Action dated Jan. 29, 2018 in corresponding Canadian application 2,888,415; 4 pages.
Notice of Acceptance dated Feb. 12, 2018 in corresponding Australian application 2013333998; 3 pages.
Arcamone, F., et al., "Stereocontrolled Glycosidation of Daunomycinone. Synthesis and Biological Evaluation of 6-Hydroxy-L-arabino Analogues of Antitumor Anthracyclines", Journal of Medicinal Chemistry, 1976, vol. 19, No. 5, pp. 733-734. (2 pages).
Argade, A.B., et al., "Marshalk Reaction Approach for a Simple Synthesis of (±)4-Demethoxydaunomy Cinone", Tetrahedron Letters, vol. 27, No. 30 pp. 3529-3532, 1986. (4 pages).
Nakai, Ken, et al., "Synthesis and antitumor activity of 5'-demethyl-5'-trifluromethyl-daunorubicin and -doxorubicin", Carbohydrate Research 320, 1999, pp. 8-18. (11 pages).

* cited by examiner

ANTHRACYCLINE DERIVATIVES FOR TREATING TUMOR DISEASES

Anthracyclines are used on a large scale in a broad spectrum of neoplastic disorders. However, the clinical use thereof is greatly limited by dose-dependent side effects and occurrence of tumor resistances. In order to get round these problems, two basic strategies have been pursued to date.

Firstly, attempts are made by "drug targeting" techniques to increase the enrichment or release of the active ingredients in the neoplastic tissue. This involves using prodrugs, wherein the anthracyclines are joined to peptides, carbohydrates, antibodies or synthetic polymers, and specific, particularly liposomal, formulations of the drugs. Examples of this are described in detail in the literature (Krohn K. "Anthracycline Chemistry and Biology II" Topics in current chemistry, 283 (2008), 73-140).

The second strategy is the design of novel anthracycline active ingredients. Since conventional anthracyclines are generally obtained by purely fermentative methods, the options for chemical modifications remain limited and are restricted to a few functional groups. Modifications are also only viable at particular positions, since the planar structure of the molecule has to be preserved in order to achieve the DNA-intercalating action. The functional groups most commonly utilized for modifications in the aglycone are the hydroxyl group at position 14, the keto group at position 13 and, in the sugar moiety, the 3'-amino group and the 4'-hydroxyl group.

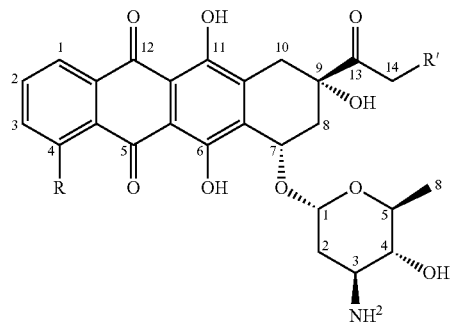

R' = H or OH
R = H or OCH$_3$

Anthracycline Base Structure

Examples of such modifications are anthracycline disaccharides, including sabarubicin, which has already been tested clinically (M. Bigioni et al., Antitumour effect of combination treatment with Sabarubicin (MEN 10755) and cis-platin (DDP) in human lung tumour xenograft, Cancer chemotherapy and pharmacology, 62 (2008) 621-629.). Further known examples of sugar-modified anthracyclines are derivatives containing a morpholino structure. The best known representative is nemorubicin, which has likewise been tested clinically (C. Sessa et al., Ongoing phase I and II studies of novel anthracyclines, Cardiovascular toxicology, 7 (2007) 75-79.).

The present invention provides novel anthracyclines having physicochemical properties, particularly basicity and hydrophilic/lipophilic balance, altered by specific structural modifications so as to control their pharmacodynamic and pharmacokinetic properties. Since structural changes in an active ingredient can severely disrupt the active ingredient-receptor interaction, the selection of the point at which the structural change is effected is of particular significance. In the compounds of the present invention, some of the structural changes are undertaken at position 6 in the sugar moiety. This position is occupied by a methyl group in the anthracyclines employed therapeutically. X-ray crystallography images showed that, in the case of the anthracyclines which act as intercalators, this sugar moiety is positioned in the "minor groove" of the DNA (C. A. Frederick et al., Structural comparison of anticancer drug-DNA complexes: adriamycin and daunomycin, Biochemistry, 29 (1990) 2538-2549.). Through the positioning of the structure-modifying moiety at position 6 of the sugar ring, it is possible to avoid disruption of the structure-activity interaction. Even sterically demanding radicals can extend into the space around the molecule without hindering intercalation. As a result of the spatial proximity to the acidic phosphate groups of the DNA in the minor groove, it is additionally possible for basic radicals to interact easily therewith.

It is a characteristic feature of the structure modifications according to the present invention that the radicals which modulate the properties of the active ingredient are bound via an oxygen, nitrogen or sulfur atom to position 6 in the sugar. The literature to date has described only halogenated derivatives at this position, and compounds having a free hydroxyl or amino group.

F. Arcamone, et al., Stereocontrolled glycosidation of daunomycinone. Synthesis and biological evaluation of 6-hydroxy-L-arabino analogues of antitumor anthracyclines, Journal of Medicinal Chemistry, 19 (1976) 733-734.

K. Nakai, et al., Synthesis and antitumor activity of 5'-demethyl-5'-trifluoromethyl-daunorubicin and -doxorubicin, Carbohydr. Res., 320 (1999) 8-18.

E. F. Fuchs, et al., New daunorubicin analogs. 3-Amino-2,3,6-trideoxy-α- and β-D-arabino- and 3,6-diamino-2,3,6-trideoxy-α-D-ribo-hexopyranosides of daunomycinone, Journal of Antibiotics, 32 (1979) 223-238.

U.S. Pat. No. 6,355,784 "Methods and compositions for the manufacture of halogenated anthracyclines with increased antitumor activity, other anthracyclines, halogenated sugars, and glycosyl donors", filed June 1999, issued March 2002.

Since a methyl group, as in the sugar moieties of the anthracyclines used therapeutically, namely acosamine and daunosamine, cannot be functionalized by known synthetic methods, the novel sugars unknown to date and derivatives thereof, and also the preparation thereof which makes it possible to obtain 6' modification of this kind, and the use thereof, also form part of the subject matter of the invention.

The present invention provides novel anthracycline derivatives of the general formula (I)

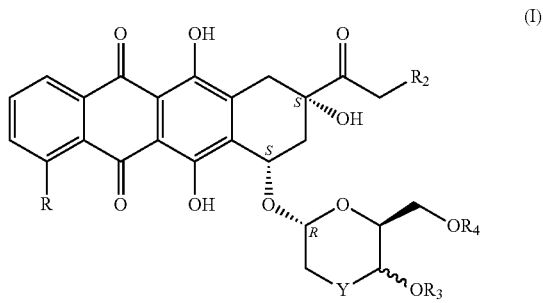

in which $R_1$ is a hydrogen atom, a hydroxyl or methoxy group, a halogen atom, especially a fluorine, chlorine or bromine atom, or an $NO_2$ group; $R_2$ is a hydrogen atom, a hydroxyl or methoxy group, an acyl or aroyl radical, preferably acetyl or benzoyl; $R_3$ is hydrogen, trifluoroacetyl $(C(=O)CF_3)$ or p-nitrobenzoyl $(C(=O)PhNO_2)$ and the wavy line in each case means both possible configurations of —$OR_3$ in relation to the base structure; $Y=[C(=O)]$, $[C(=N)—OH]$ or $[CH—OH]$, $[CH—NR_5R_6]$ in both possible stereoisomeric arrangements, but is preferably $[CH—NR_5R_6]$, where $R_5$ and $R_6$ are preferably the same and are each a hydrogen atom, but may also be different and may be a hydrogen atom or an amino protecting group, preferably a trifluoroacetyl group (TFA); in which $X=O$, S or NR with R=hydrogen or $C_1$ to $C_4$ alkyl, preferably methyl, ethyl, propyl and tert-butyl or n-butyl, most preferably methyl or ethyl; in which $R_4$ is an unbranched or branched alkyl or heteroalkyl chain having a chain length of 1 to 19 elements, where a maximum of 6 heteroatoms (O, N, S) in any combination are separated from one another by at least two carbon atoms. Preferably, $R_4$ is a $(CH_2—CH_2—O)_n$— group with n=1 to 6, with a hydrogen atom or a $C_1$ to $C_4$ alkyl group, preferably methyl, ethyl, propyl and tert-butyl or n-butyl, most preferably a methyl or ethyl group, bonded to the terminal oxygen atom of the $(CH_2—CH_2—O)_n$— group.

Suitable protecting groups, especially for the amino group, are known to those skilled in the art from the prior art, for example from "Protective Groups in Organic Synthesis" (Greene, Wuts) 4th edition, John Wiley & Sons, Inc., pages 781 to 783.

In a preferred embodiment, according to formula (Ia),

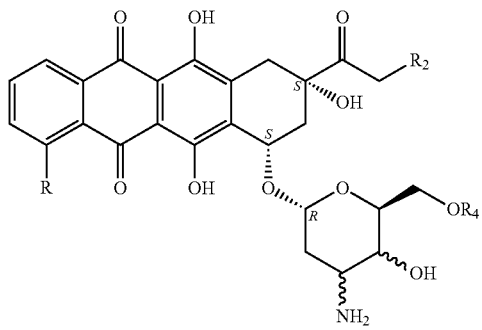

(Ia)

in which $R_1$ is a hydrogen atom, a hydroxyl or methoxy group, a halogen atom, especially a fluorine, chlorine or bromine atom, or an $NO_2$ group; $R_2$ is a hydrogen atom, a hydroxyl or methoxy group, an acyl or aroyl radical, preferably acetyl or benzoyl; the amino group and also the hydroxyl group may be present in either possible stereochemical arrangement; $R_4$ is defined as the $(CH_2—CH_2—O)_n$— group with n=1 to 6, preferably n=3, 4 or 5, and in which there is a hydrogen atom or a $C_1$ to $C_4$ alkyl group, preferably methyl, ethyl, propyl and tert-butyl or n-butyl, on the terminal oxygen atom of the chain, most preferably a methyl group or ethyl group bonded to the terminal oxygen atom of the chain.

The present invention further provides a process for preparing the anthracycline derivatives of the general formula (I), wherein an open-chain sugar compound of the general formula (II)

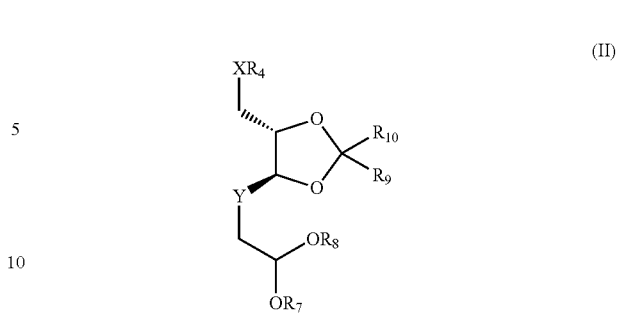

(II)

in which $R_7$ and $R_8$ are the same and are each alkyl or alkylene having 2 to 3 carbon atoms; $R_9$ and $R_{10}$ are each an alkyl group having 1 to 3 carbon atoms; X, Y and $R_4$ are each as defined in formula (I) is cyclized. For a compounds of the general formula (II) to be intramolecularly cyclized, the diol and aldehyde protecting group has to be cleaved; this is accomplished under acidic conditions, preferably in a mixture of trifluoroacetic acid in tetrahydrofuran/water as solvent at a temperature of about 20° C. to 100° C., preferably at 55 to 65° C. The resulting pyranose of the general formula (III)

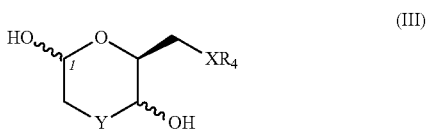

(III)

in which X, Y and $R_4$ are each as defined in formula (I) forms as a mixture of the two anomers at position 1 in the general formula (III), which need not be separated since both anomers are suitable for the glycosylation. Subsequently, compounds of the general formula (III) are glycosylated with a tetracyclic aglycone of the anthracycline (AA) structure type. Preferably, AA is an intercalatable tetracyclic aglycone of the anthracycline structure type.

A number of reactions may be used as the glycosylation reaction. The compound III can be used directly in the reaction or can preferably be activated beforehand for the glycosylation. This activation is preferably conducted with p-nitrobenzoyl chloride in pyridine at a temperature of −10° C. to 50° C., preferably at about 0° C. This reaction leads to compounds of the general formula (IIIa). Likewise of good suitability for activation is trifluoroacetic anhydride in diethyl ether, in which case the reaction is conducted at from −10° C. to 50° C., preferably at about 0° C., and gives compounds of the general formula (IIIb)

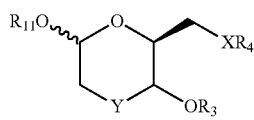

(IIIa): $R_3$, $R_{11}$ = $C(=O)PhNO_2$
(IIIb): $R_3$, $R_{11}$ = TFA

In IIIa and IIIb, X, Y and $R_4$ are each as defined in formula (I).

The glycosylation with a tetracyclic aglycone of the anthracycline (AA) structure type leads to a compound of the general formula IIIc

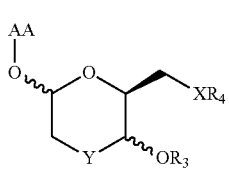

(IIIc)

in which AA is a tetracyclic aglycone of the anthracycline structure type, preferably an intercalatable tetracyclic aglycone, and X, Y, $R_3$ and $R_4$ are each as defined in formula I.

The subsequent detachment of the protecting groups can be conducted by methods described in detail in the literature (T. Matsumoto, M. Osaki, K. Yamada, F. Matsuda, S. Terashima, 14-Fluoroanthracyclines. Novel syntheses and antitumor activity, Chemical & Pharmaceutical Bulletin, 36 (1988) 3793-3804); (Y. Kimura, M. Suzuki, T. Matsumoto, R. Abe, S. Terashima, Novel glycosidation of 4-demethoxyanthracyclinones by the use of trimethylsilyl triflate. Syntheses of optically active 4-demethoxydaunorubicin and 4-demethoxyadriamycin, Bulletin of the Chemical Society of Japan, 59 (1986) 423-431).

In the preferred embodiment, the activated pyranoses of the general formula (IIIa) or (IIIb) are reacted in a glycosidation reaction with an anthraquinone-derived aglycone of the general formula (IV)

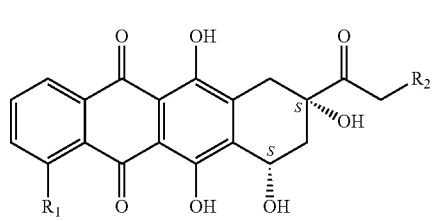

(IV)

in which $R_1$ is a hydrogen atom, a hydroxyl or methoxy group, a halogen atom, especially a fluorine, chlorine or bromine atom, or an $NO_2$ group; $R_2$ is a hydrogen atom, a hydroxyl or methoxy group, an acyl or aroyl radical, preferably acetyl or benzoyl, wherein a reaction activation is effected. For example, reaction activation is effected by using trimethylsilyl trifluoromethanesulfonate (TMSOTf) in a mixture of dichloromethane/diethyl ether at temperatures of about 0 to −70° C., preferably between 0 and −20° C. The protecting groups still present on the sugar [TFA, C(=O)PhNO$_2$] can be detached under basic conditions, preferably with sodium hydroxide solution, giving compounds of the general formula (Ia)

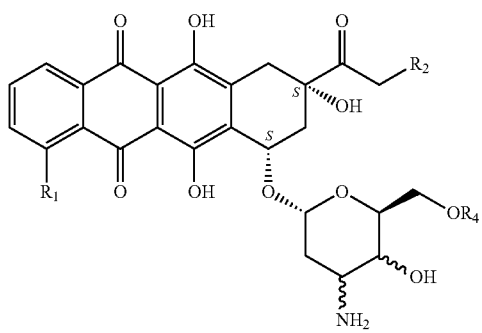

(Ia)

in which $R_1$ is a hydrogen atom, a hydroxyl or methoxy group, a halogen atom, especially a fluorine, chlorine or bromine atom, or an $NO_2$ group; $R_2$ is a hydrogen atom, a hydroxyl or methoxy group, an acyl or aroyl radical, preferably acetyl or benzoyl, $R_4$ is defined as —(CH$_2$—CH$_2$—O)$_n$— with n=1 to 6, preferably n=3, 4 and 5, and in which there is a hydrogen atom or a $C_1$ to $C_4$ alkyl group, preferably methyl, ethyl, propyl and tert-butyl or n-butyl, most preferably a methyl group or ethyl group, on the terminal oxygen atom of the chain.

The open-chain sugar compounds of the general formula (II), together with the processes for preparation thereof, form a further part of the subject matter of the present invention.

Open-chain sugar compounds of the general formula (II)

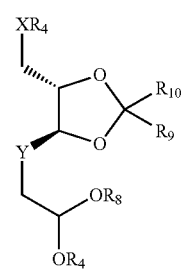

(II)

can be prepared by total synthesis, preferably employing the addition of a C2 unit of the general formula (V)

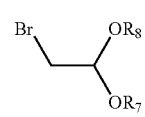

(V)

in which $R_7$ and $R_8$ are each as defined in formula (II) with a protected derivative of L-threose (enantiomerically pure C4 unit) of the general formula (VI)

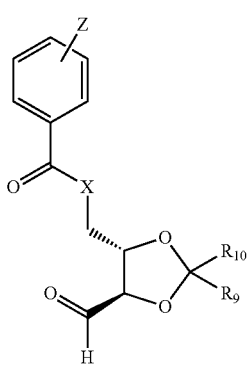

(VI)

in which X, $R_9$, $R_{10}$ are each as defined in formula (II) and Z=hydrogen, or at least or two or more, preferably one or two, methyl, fluorine, chlorine, bromine or nitro groups.

Compounds of the general formula (VI) in which X=O and $R_9$ and/or $R_{10}$ is a methyl group have been described in detail in the literature (S. Morgenlie, Identification of the products of periodate oxidation of some mono-O-isopropylidene derivatives of aldoses and alditols by g.l.c.-m.s, Carbohydr. Res., 138 (1985) 329-334); (N. Cohen, B. L. Banner, R. J. Lopresti, Synthesis of optically active leukotriene (SRS-A) intermediates, Tetrahedron Letters, 21 (1980) 4163-4166).

The C—C bond between compounds of the general formula (V) and compounds of the general formula (VI) is preferably formed by a Grignard reaction, preferably in an aprotic solvent such as tetrahydrofuran, methyl tert-butyl ether or diethyl ether at a temperature of about 0° C. to 100° C., preferably at room temperature, forming compounds of the general formula (VII)

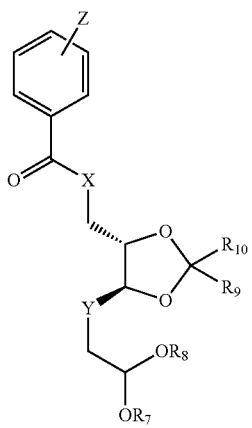

(VII)

in which $R_7$, $R_8$, $R_9$, $R_{10}$ are each as defined in formula (II); X, $R_9$, $R_{10}$ are each as defined in formula (II) and Z=hydrogen, or at least or more than one, preferably one or two, methyl, fluorine, chlorine, bromine or nitro groups, and Y=CH—OH in both possible stereoisomeric arrangements.

This addition product is subsequently oxidized to the ketone [Y=C(=O)] of the general formula (VII), preferably by a Swern oxidation in dichloromethane at low temperatures, preferably at −50° C. to −90° C., most preferably at −60° C.

Various methods are available for introduction of the nitrogen into the molecule. The best way is to effect this reaction by converting the ketone [Y=C(=O)] of the general formula (VII) to an oxime [Y=C(=N)—OH] of the general formula (VII), preference being given to conducting this reaction with hydroxylamine hydrochloride, preferably in pyridine at 20° C. to 80° C., most preferably at about 55° C.

Subsequently, the aroyl protecting group on X is detached, preferably in a basic medium, preferably by means of NaOH in THF/$H_2O$. After the elimination, an R4 radical as defined in formula I is introduced, the introduction of an unbranched or branched alkyl or heteroalkyl chain on X preferably being effected by nucleophilic substitution, more preferably with the aid of a non-nucleophilic base, such as sodium hydride, in THF or DMF, and the R4 radical to be introduced being activated beforehand. For activation, preference is given to using a tosylate radical as leaving group, for example para-toluenesulfonyl chloride, NaOH and tetrahydrofuran/water at temperatures of 0° C. to 60° C.

The resultant oxime [Y=C(=N)—OH] of the general formula (II) is reduced to the amine [Y=CH—$NH_2$] of the general formula (II). A multitude of reagents are available for this reaction, and those of particularly good suitability include chiral and non-chiral metal hydrides such as sodium bis(2-methoxyethoxy)aluminum dihydride or $LiAlH_4$. Preferably, this reaction is conducted with sodium bis(2-methoxyethoxy)aluminum dihydride or $LiAlH_4$ in toluene or THF at 0° C. to 100° C., preferably at room temperature.

The resulting amino group is in turn provided with a protecting group suitable for selective detachment after ring closure and glycosylation, the trifluoroacetyl group being particularly suitable for this purpose, and it being possible to conduct the reaction with trifluoroacetic anhydride in pyridine as solvent, preferably at 0° C. to 60° C., preferably at room temperature, thus forming a sugar compound of the general formula (II) [Y=CH—$NR_5R_6$] in which $R_5/R_6$ are different and are each as defined in formula (I).

The present invention further provides a process for preparing anthraquinone-derived aglycones of the general formula (IV)

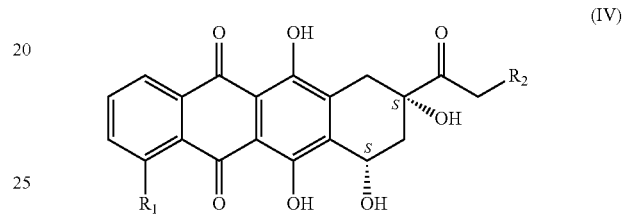

(IV)

which are prepared by total synthesis, in its preferred embodiment by conducting the stereoselective alkylation based on the Seebach reaction (Seebach, D.; Sting, A. R.; Hoffmann, M. *Angewandte Chemie, International Edition in English* 1997, 35, 2708), while the Marschalk reaction is employed in the cyclization (Marschalk, C.; Koenig, F.; Ouroussoff, N. *Bulletin de la Société Chimique de France, Memoires* 1936, 3, 1545).

The ring system is prepared by the reaction of a tricyclic bromide of the general formula (VIII)

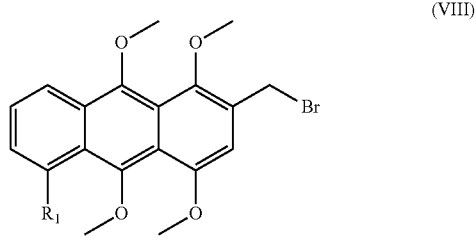

(VIII)

in which $R_1$ is as defined in formula (I)
with a synthon of the general formula (IX)

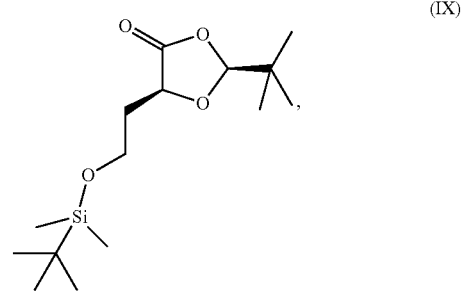

(IX)

wherein the compound of the general formula (IX) is first deprotonated with a non-nucleophilic base, for example LDA (lithium diisopropylamide), LiHMDS (lithium bis(trimethylsilyl)amide), but preferably with KHMDS (potassium bis(trimethylsilyl)amide), in a polar aprotic solvent (e.g. dimethylformamide or tetrahydrofuran). The reaction is effected preferably at −40° C. to −90° C., most preferably at −60° C. to −80° C., the very most preferably at −76° C.

The subsequent alkylation leads to the formation of an enantiomerically pure compound of the general formula (X)

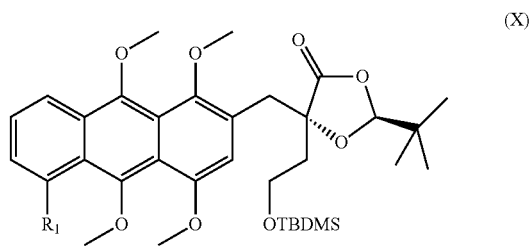

(X)

in which $R_1$ is a hydrogen atom, a hydroxyl or methoxy group, a halogen atom, especially a fluorine, chlorine or bromine atom, or an $NO_2$ group.

The reaction of a compound of the general formula (X) with an organometallic reagent such as organomagnesium, -lithium or -sodium, preferably with methyllithium, in an aprotic solvent, for example tetrahydrofuran, at −40° C. to −90° C., preferably at −50° C. to −80° C., most preferably at −78° C., gives a compound of the formula (XI)

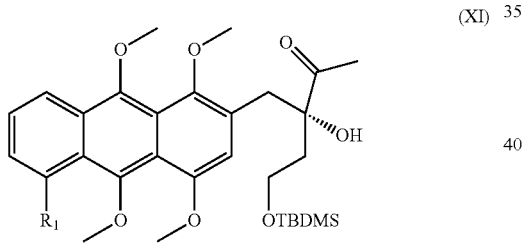

(XI)

in which $R_1$ is a hydrogen atom, a hydroxyl or methoxy group, a halogen atom, especially a fluorine, chlorine or bromine atom, or an $NO_2$ group.

The keto group in the compound of the general formula (XI) is reduced in a reduction reaction, preferably a hydride reduction, for example with sodium borohydride in ethanol as solvent, preferably at 10° C. to 70° C., preferably at room temperature, to a hydroxyl group and then is ketalized to give a compound of the general formula (XII)

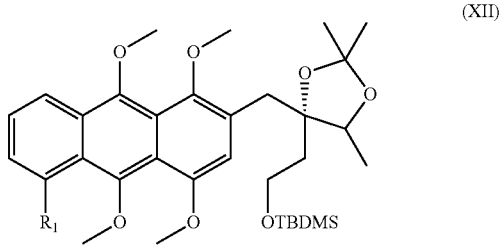

(XII)

in which $R_1$ is a hydrogen atom, a hydroxyl or methoxy group, a halogen atom, especially a fluorine, chlorine or bromine atom, or an $NO_2$ group.

The ketalization can preferably be conducted with dimethoxypropane and p-toluenesulfonic acid in acetone. After the cleavage of the silyl protecting group, which is best effected with a fluoride reagent, for example tetrabutylammonium fluoride (TBAF) in THF, preferably at room temperature, the hydroxyl group released is oxidized to the aldehyde of the general formula (XIII)

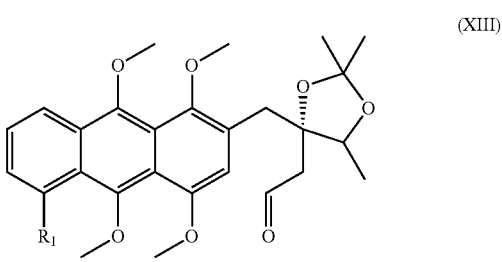

(XIII)

in which $R_1$ is a hydrogen atom, a hydroxyl or methoxy group, a halogen atom, especially a fluorine, chlorine or bromine atom, or an $NO_2$ group; preferably by a Swern oxidation.

The compound of the general formula (XIII) thus obtained is converted by oxidative dealkylation preferably employing a cerium salt (cerium(IV) ammonium nitrate, preferably in acetonitrile at 0° C. to 10° C., most preferably at about 2° C.) to the anthraquinone derivative of the general formula (XIV)

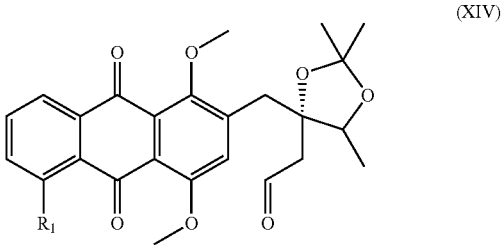

(XIV)

in which $R_1$ is a hydrogen atom, a hydroxyl or methoxy group, a halogen atom, especially a fluorine, chlorine or bromine atom, or an $NO_2$ group.

The remaining protecting groups (e.g. methoxy and acetonide) are detached under acidic conditions, for which purpose preference is given to using Lewis acids such as $BBr_3$ (boron tribromide), $BI_3$ (boron triiodide), $BF_3$ (boron trifluoride) or $AlCl_3$ (aluminum chloride), preferably $BCl_3$ (boron trichloride) in DCM, preferably at 0° C.-10° C., most preferably at about 2° C., giving the hemiacetal of the general formula (XV)

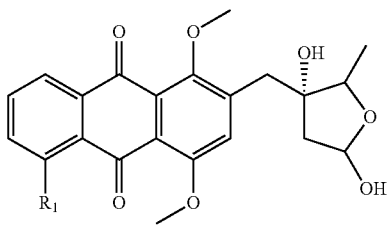

(XV)

in which $R_1$ is a hydrogen atom, a hydroxyl or methoxy group, a halogen atom, especially a fluorine, chlorine or bromine atom, or an $NO_2$ group.

Formula (XV) is subsequently cyclized, preferably with the aid of a Marschalk reaction in tetrahydrofuran/methanol as solvents, preferably in a temperature range from $-10°$ C. to room temperature, to give the compound of the general formula (XVI)

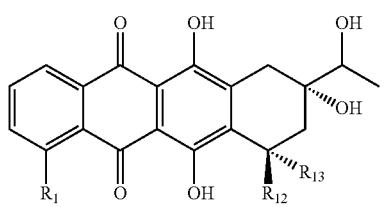

(XVI)

in which $R_1$ is a hydrogen atom, a hydroxyl or methoxy group, a halogen atom, especially a fluorine, chlorine or bromine atom, or an $NO_2$ group, $R_{12}$ and $R_{13}$ are each a hydrogen atom, or are one hydrogen atom and one hydroxyl group in any combination.

The side chain hydroxyl group is subsequently oxidized, for which purpose Dess-Martin periodinane is particularly suitable, preferably at room temperature, in order thus to obtain a compound of the general formula (XVII)

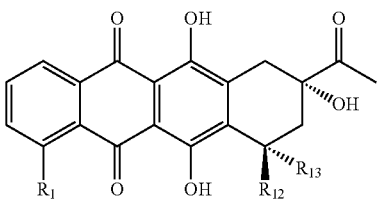

(XVII)

in which $R_1$ is a hydrogen atom, a hydroxyl or methoxy group, a halogen atom, especially a fluorine, chlorine or bromine atom, or an $NO_2$ group, $R_{12}$ and $R_{13}$ are each a hydrogen atom, or are one hydrogen atom and one hydroxyl group in any combination.

The compound of the formula (XVII), provided that $R_{12}$ and $R_{13}$ are each a hydrogen atom, is then hydroxylated, for which purpose N-bromosuccinimide and azobis(isobutyronitrile) in $CCL_4$ are particularly suitable, preference being given to effecting the hydroxylation under reflux, to form a compound of the general formula (IV) in which $R_1$ is a hydrogen atom, a hydroxyl or methoxy group, a halogen atom, especially a fluorine, chlorine or bromine atom, or an $NO_2$ group, and $R_2$ is hydrogen

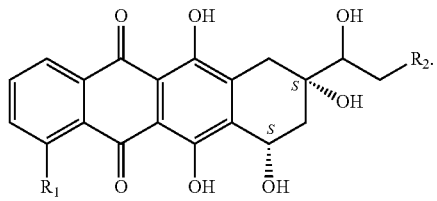

(IV)

Compounds of the general formula (I), (Ia) and (IIIc) of the present invention, in non-radioactive cell proliferation and cytotoxicity tests on tumor cell lines, for example the two tumor cell lines MCF-7 and KB-3-1, show statistically significant effects in terms of their cytotoxic effect and their propensity to inhibit cell proliferation.

Accordingly, the present invention further relates to pharmaceutical composition comprising one or more compounds of the formula (I), (Ia) and (IIIc) and optionally one or more pharmaceutically acceptable substances selected from auxiliaries, carriers, diluents and solvents.

Suitable auxiliaries, carriers, diluents and solvents are known to those skilled in the art.

The present invention further relates to a pharmaceutical kit comprising (i) one or more compounds of the formula (I), (Ia) and (IIIc), or a pharmaceutical composition comprising one or more compounds of the formula (I), (Ia) and (IIIc) and optionally one or more pharmaceutically acceptable substances selected from auxiliaries, carriers, diluents and solvents, and (ii) at least one antiproliferative or cytotoxic active ingredient.

The compounds of the formula (I), (Ia) and (IIIc), a pharmaceutical composition or a pharmaceutical kit according to the present invention can be used as a medicament or as a tool in biomedical research.

Compounds of the formula (I), (Ia) and (IIIc), a pharmaceutical composition or a pharmaceutical kit according to the present invention can additionally be used for treatment of diseases or disease states which can be at least partly alleviated by therapy. The diseases or disease states are selected from proliferative diseases, preferably cancer.

The compounds of the formula (I), (Ia) and (IIIc), a pharmaceutical composition or a pharmaceutical kit according to the present invention can be used as single-drug preparations or in combination with other active ingredients, preferably active ingredients which likewise inhibit cell proliferation or can display a cytotoxic effect. Examples include the known active ingredients bleomycin, vinblastin, dacarbazine, cyclophosphamide, etoposide (phosphate), procarbazine, vincristin, prednisone, cisplatin, carboplatin, 5-fluorouracil, docetaxel, which even now are being used in combination with anthracyclines (e.g. ABVD, BEACOPP, ECF, TAC, TEC).

It is likewise possible to use the compounds of the formula (I), (Ia) and (IIIc) of the present invention together with recombinant active ingredients (biologics) which can enhance the effect of the inventive compounds in a specific manner, for example as antibodies.

The present invention is now illustrated in detail by the examples which follow.

EXAMPLE 1

N-[(2S,3S,4S)-3,6-dihydroxy-2-[2-[2-[2-[2-(2-methoxy-ethoxy)ethoxy]ethoxy]ethoxy]ethoxymethyl]tetrahydropyran-4-yl]-2,2,2-trifluoroacetamide; formula (III); $R_4$=[(—$CH_2$—$CH_2$—O)$_5$—$CH_3$]; X=O; Y=[CH—$NR_5R_6$], $R_5$=H, $R_6$=[C(=O)$CF_3$]

To a solution of 8.9 g (17.2 mmol) of N-[2-(1,3-dioxolan-2-yl)-1-[(4S,5S)-5-[2-[2-[2-[2-(2-methoxy-ethoxy)ethoxy]ethoxy]ethoxy]ethoxymethyl]-2,2-dimethyl-1,3-dioxolan-4-yl]ethyl]-2,2,2-trifluoroacetamide (II) in THF/$H_2O$ (4:1) are added dropwise 43 mL (0.56 mol) of trifluoroacetic acid. Subsequently, the mixture is stirred at 60° C. for 30 min. Then the reaction mixture is emptied onto 100 mL of ice-water and 87 g (1.03 mol) of solid $NaHCO_3$ are added until pH 6-7 is attained. The reaction mixture is subsequently filtered and extracted with 3× with 200 mL of dichloromethane each time. The combined organic phases are dried over sodium sulfate, filtered and concentrated by evaporation. The resultant oil is purified by chromatography (eluent: DCM/MeOH 100:3→100:5→10:1, v/v). 2.1 g (27%) of colorless oil are isolated. The anomeric ratio is α:β=76:24.

$^1$H NMR (α), (500 MHz; $CDCl_3$): δ (ppm)=7.09 (m, 1H, NH); 5.41 (m, 1H, H-1); 4.47 (m, 1H, H-3); 4.18 (m, 1H, H-5); 3.92 (m, 1H, H-4); 3.79-3.69 (m, 2H, H-6/1, H-6/2); 3.62 (m, 18H, $CH_2O$); 3.55 (m, 2H, $MeOCH_2$); 3.35 (s, 3H, OMe); 2.00-1.91 (m, 1H, H-2/1); 1.87-1.84 (m, 1H, H-2/2)

$^1$H NMR (β), (500 MHz; $CDCl_3$): δ (ppm)=7.29 (m, 1H, NH); 5.18 (m, 1H, H-1); 4.16-4.06 (m, 1H, H-3); 3.82 (m, 1H, H-4); 3.79-3.69 (m, 2H, H-6/1, H-6/2); 3.62 (m, 19H, $CH_2O$, H-5); 3.55 (m, 2H, $CH_2O$); 3.35 (s, 3H, OMe); 2.04-2.00 (m, 1H, H-2/1); 1.80-1.74 (m, 1H, H-2/2).

EXAMPLE 2

[(4S,5S,6S)-6-[2-[2-[2-[2-(2-methoxyethoxyl)ethoxy]-ethoxy]ethoxy]ethoxymethyl]-5-(4-nitrobenzoyl)oxy-4-[(2,2,2-trifluoroacetyl)amino]tetrahydropyran-2-yl]4-nitrobenzoate; formula (IIIa); $R_3$=$R_{11}$=[C(=O)Ph$NO_2$]; $R_4$=[(—$CH_2$—$CH_2$—O)$_5$—$CH_3$]; X=O; Y=[CH—$NR_5R_6$], $R_5$=H, $R_6$=[C(=O)$CF_3$]

To a solution of 1.67 g (3.38 mmol) of N-[(3S,4S,6S)-3,6-dihydroxy-2-[2-[2-[2-[2-(2-methoxy-ethoxy)ethoxy]ethoxy]ethoxy]ethoxymethyl]tetrahydropyran-4-yl]-2,2,2-trifluoroacetamide (II) in pyridine is cooled to 0° C. under inert gas. Subsequently, 1.75 g (9.43 mmol) of p-nitrobenzoyl chloride are added and the reaction mixture is warmed to room temperature within 12 h. The reaction is quenched with $H_2O$ and then all solvents are evaporated off. The residue is taken up in dichloromethane and washed once $H_2O$, three times with semisaturated $NaHCO_3$ solution and once with saturated NaCl solution, dried over sodium sulfate, filtered and concentrated by evaporation. The resulting oil is purified by chromatography (eluent: ethyl acetate/petroleum ether 1:1→3:2→2:1, v/v). 1.94 g (72%) are obtained as a white foam. The anomeric ratio is α:β=76:24.

$^1$H NMR (α), (200 MHz; $CDCl_3$): δ (ppm)=8.30 (m, 8H, Ar); 6.88 (d, 1H, J=6.56 Hz, NH); 6.67 (m, 1H, H-1); 5.76 (m, 1H, H-4); 4.80 (m, 1H, H-5); 4.46 (m, 1H, H-3); 3.63-3.46 (m, 22H, H-6/1, H-6/2, $CH_2O$); 3.34 (s, 3H, OMe); 2.39-2.33 (m, 2H, H-2/1, H-2/2)

$^1$H NMR (β), (200 MHz; $CDCl_3$): δ (ppm)=8.28 (m, 8H, Ar); 6.90 (m, 1H, NH); 6.15 (m, 1H, H-1); 5.64 (m, 1H, H-4); 4.51 (m, 1H, H-5); 4.18 (m, 1H, H-3); 3.69-3.52 (m, 22H, H-6/1, H-6/2, $CH_2O$); 3.34 (s, 3H, OMe); 2.44-2.17 (m, 2H, H-2/1, H-2/2).

EXAMPLE 3

[(2S,3S,4S,6R)-6-[[(1S,3S)-3-acetyl-3,5,12-trihydroxy-10-methoxy-6,11-dioxo-2,4-dihydro-1H-tetracen-1-yl]-oxy]-2-[2-[2-[2-[2-(2-methoxyethoxyl)ethoxy]ethoxy]-ethoxy]ethoxymethyl]-4-[(2,2,2-trifluoroacetyl)amino]-tetrahydropyran-3-yl]4-nitrobenzoate; formula (I); $R_1$=OMe; $R_2$=H; $R_3$=[C(=O)Ph$NO_2$]; $R_4$=[(—$CH_2$—$CH_2$—O)$_5$—$CH_3$]; X=O; Y=[CH—$NR_5R_6$], $R_5$=H, $R_6$=[C(=O)$CF_3$]

To a solution of 225 mg (0.28 mmol) [(4S,5S,6S)-6-[2-[2-[2-[2-(2-methoxyethoxyl)ethoxy]ethoxy]ethoxy]-ethoxymethyl]-5-(4-nitrobenzoyl)oxy-4-[(2,2,2-trifluoroacetyl)amino]tetrahydropyran-2-yl]4-nitrobenzoate, (III), in 15 mL of dichloromethane and 12 mL of $Et_2O$ are added 1.1 g of 4 A molecular sieve. Under inert gas, 129 mg (0.58 mmol) of trimethylsilyl trifluoromethanesulfonate are added dropwise at −40° C. and the mixture is stirred at 0° C. for 1 h, the mixture is cooled to −20° C. and 56 mg (0.14 mmol) of (7S,9S)-9-acetyl-6,7,9,11-tetrahydroxy-4-methoxy-8,10-dihydro-7H-tetracene-5,12-dione, (IV), dissolved in 9 mL of tetrahydrofuran, are added dropwise. Subsequently, the mixture is stirred at −10° C. to −15° C. for 6 h. Added to the reaction mixture are saturated $NaHCO_3$ solution and dichloromethane, and the phases are separated. The aqueous phase we extracted repeatedly with dichloromethane. The combined organic phases are washed with $H_2O$ and saturated NaCl solution, dried over sodium sulfate, filtered and concentrated by evaporation. The resulting residue is purified by chromatography (eluent: DCM/MeOH 100:1→100:2→100:4, v/v). 118 mg (82%) of orange-red solid are obtained.

$^1$H NMR (500 MHz, $CDCl_3$): δ (ppm)=13.93 (s, 1H, OH-6); 13.15 (s, 1H, OH-11); 8.30-8.23 (m, 4H, Ar); 7.90 (d, 1H, J=7.55 Hz, H-1); 7.76-7.72 (m, 1H, H-2); 7.35 (d, 1H, J=8.5 Hz, H-3); 6.72 (m, 1H, NH); 5.69 (m, 1H, H-1'); 5.62 (m, 1H, H-4'); 5.20 (m, 1H, H-7); 4.56-4.53 (m, 1H, H-5'); 4.48-4.40 (m, 1H, H-3'); 4.04 (s, 3H, ArOMe); 3.68-3.45 (m, 22H, $CH_2O$, H-6); 3.33 (s, 3H, OMe); 3.12 (m, 1H, H-10/1); 2.88 (m, 1H, H-10/2); 2.57 (m, 1H, H-8/1); 2.43 (s, 3H, H-14); 2.18-2.02 (m, 3H, H-8/2, H-2')

EXAMPLE 4

N-[(2S,3S,4S,6R)-6-[[(1S,3S)-3-acetyl-3,5,12-trihydroxy-10-methoxy-6,11-dioxo-2,4-dihydro-1H-tetracen-1-yl]oxy]-3-hydroxy-2-[2-[2-[2-(2-methoxy-ethoxy)ethoxy]ethoxy]ethoxy]ethoxymethyl]tetrahydropyran-4-yl]-2,2,2-trifluoroacetamide; formula (I); $R_1$=OMe; $R_2$=$R_3$=H; $R_4$=[(—$CH_2$—$CH_2$—O)$_5$—$CH_3$]; X=O; Y=[CH—$NR_5R_6$], $R_5$=H, $R_6$=[C(=O)$CF_3$]

A solution of 99 mg (0.1 mmol) of [(2S,3S,4S,6R)-6-[[(1S,3S)-3-acetyl-3,5,12-trihydroxy-10-methoxy-6,11-dioxo-2,4-dihydro-1H-tetracen-1-yl]oxy]-2-[2-[2-[2-[2-(2-methoxyethoxyl)ethoxy]ethoxy]ethoxy]ethoxymethyl]-4-[(2,2,2-trifluoroacetyl)amino]tetrahydropyran-3-yl]4-nitrobenzoate, (I), in 52.1 mL of methanol and 0.1 mL of dichloromethane is cooled to 0° C. Subsequently, 1.3 mL of 0.1 N NaOH are added dropwise and the mixture is stirred at 0° C. for 30 min. The reaction mixture we then neutralized with glacial acetic acid, and ethyl acetate and saturated NaCl solution are added. The phases are separated and the aqueous phase is extracted once with ethyl acetate. The combined organic phases are washed with saturated NaCl solution, dried over sodium sulfate, filtered and concentrated by evaporation. The resultant residue is purified by chromatography (eluent: DCM/MeOH 100:4, v/v). 75.9 mg (89%) of orange-red solid are obtained.

$^1$H NMR (500 MHz, CDCl$_3$): δ (ppm)=13.94 (s, 1H, OH-6); 13.23 (s, 1H, OH-11); 7.99 (d, 1H, J=7.55 Hz, H-1); 7.75 (t, 1H, J=8.02 Hz, H-2); 7.36 (d, 1H, J=8.5 Hz, H-3); 7.10 (m, 1H, NH); 5.56 (m, 1H, H-1'); 5.25 (m, 1H, H-7); 4.22-4.14 (m, 1H, H-3'); 4.14-4.11 (m, 1H, H-5'); 4.05 (s, 3H, ArOMe); 3.98 (m, 1H, H-4'); 3.87-3.71 (m, 2H, H-6/1, H-6/2); 3.69-3.53 (m, 20H, CH$_2$O); 3.35 (s, 3H, OMe); 3.27-3.17 (m, 1H, H-10/1); 2.87-2.84 (m, 1H, H-10/2); 2.39 (s, 3H, H-14); 2.37-2.34 (m, 1H, H-8/1); 2.12-2.01 (m, 2H, H-8/2, H-2'/1); 1.86-1.83 (m, 1H, H-2'/2)

EXAMPLE 5

(7S,9S)-9-acetyl-7-[(2R,4S,5S,6S)-4-amino-5-hydroxy-6-[2-[2-[2-[2-(2-methoxyethoxy)ethoxy]ethoxy]ethoxy]-ethoxymethyl]tetrahydropyran-2-yl]oxy-6,9,11-trihydroxy-4-methoxy-8,10-dihydro-7H-tetracene-5,12-dione; formula (I); R$_1$=OMe; R$_2$=R$_3$=H; R$_4$=[(—CH$_2$—CH$_2$—O)$_5$—CH$_3$]; X=O; Y=[CH—NH$_2$]

A solution of 60 mg (0.07 mmol) of N-[(2S,3S,4S,6R)-6-[[(1S,3S)-3-acetyl-3,5,12-trihydroxy-10-methoxy-6,11-dioxo-2,4-dihydro-1H-tetracen-1-yl]-oxy]-3-hydroxy-2-[2-[2-[2-[2-(2-methoxyethoxy)ethoxy]-ethoxy]ethoxy]ethoxymethyl]tetrahydropyran-4-yl]-2,2,2-trifluoroacetamide, (I), in 12.5 mL of 1 N NaOH is stirred at room temperature for 20 min. The reaction mixture is subsequently neutralized with 12.5 mL of 1N HCl and extracted with dichloromethane until the extracts no longer have any orange color. The combined organic phases are washed with saturated NaCl solution, dried over sodium sulfate, filtered and concentrated by evaporation. The resulting residue is purified by chromatography (eluent: DCM/MeOH 10:1→10:2, v/v). 13 mg (24%) of orange-red solid are obtained.

$^1$H NMR (500 MHz, CDCl$_3$): δ (ppm)=13.81 (s, 1H, OH-6); 13.12 (s, 1H, OH-11); 7.85 (d, 1H, J=6.9 Hz, H-1); 7.67 (t, 1H, J=7.57 Hz, H-2); 7.36 (m, 1H, H-3); 5.52 (m, 1H, H-1'); 5.00 (m, 1H, H-7); 4.27 (m, 1H, H-4'); 4.19 (m, 1H, H-5'); 3.95 (s, 3H, ArOMe); 3.91-3.50 (m, 23H, H-3', H-6', CH$_2$O); 3.33 (s, 3H, OMe); 3.13-3.10 (m, 1H, H-10/1); 2.81-2.77 (m, 1H, H-10/2); 2.38 (s, 3H, H-14); 2.35 (m, 1H, H-8/1); 2.18-2.00 (m, 3H, H-2', H-8/2)

EXAMPLE 6

[(4S,5S)-5-[2-(1,3-dioxolan-2-yl)-1-hydroxyethyl]-2,2-dimethyl-1,3-dioxolan-4-yl]methyl benzoate; formula (VII); R$_7$=R$_8$=CH$_2$; R$_9$=R$_{10}$=CH$_3$; X=O; Y=[CH—OH]

A solution of 4.20 g (0.17 mol) of magnesium turnings and 2 mg (0.015 mmol) of elemental iodine in 200 mL of THF is heated to boiling under argon for 10 min. Subsequently, 26 g (0.15 mol) of 2-bromomethyl-1,3-dioxolane (V) are added dropwise until the onset of the reaction becomes apparent. The rest of the 2-bromomethyl-1,3-dioxolane (V) is metered in subsequently such that the reaction mixture boils gently. After the addition has ended, the reaction mixture is stirred at 80° C. for 2 h. Thereafter, 20 g (0.08 mol) of [(4S,5R)-5-formyl-2,2-dimethyl-1,3-dioxolan-4-yl]methyl benzoate (VI), dissolved in 30 mL of THF, are added dropwise to the reaction mixture and the mixture is stirred at room temperature for 6 h. 200 mL of saturated NH$_4$Cl solution and 200 mL of ice are added to the reaction mixture, which is stirred for 5 min. Subsequently, 300 mL of ethyl acetate are added, phases are separated and the aqueous phase is extracted with 100 mL of ethyl acetate. The combined organic phases are washed with 100 mL of saturated NH$_4$Cl solution, dried over Na$_2$SO$_4$, filtered and concentrated by evaporation. 25 g (92%) of yellow oil (51:49 mixture of the diastereomers of 3') are obtained.

$^1$H NMR (diastereomer 1), (500 MHz, CDCl$_3$): δ (ppm)=8.06 (m, 2H, Ar); 7.56 (m, 1H, Ar); 7.44 (m, 2H, Ar); 5.09 (m, 1H, H-1); 4.66 (dd, J1=11.6 Hz, J2=2.5 Hz, 1H, H-6/1); 4.39 (dd, J1=11.6 Hz, J2=5.6 Hz, 1H, H-6/2); 4.31 (m, 1H, H-5); 4.08-3.80 (m, 6H, H-4, H-3, 2×OCH$_2$); 2.18-2.14 (m, 1H, H-2/1); 1.90-1.81 (m, 1H, H-2/2); 1.42 (s, 3H, MeC); 1.41 (s, 3H, MeC)

$^1$H NMR (diastereomer 2), (500 MHz, CDCl$_3$): δ (ppm)=8.06 (m, 2H, Ar); 7.56 (m, 1H, Ar); 7.44 (m, 2H, Ar); 5.09 (m, 1H, H-1); 4.55 (m, 1H, H-6/1); 4.48-4.31 (m, 2H, H-6/2, H-5); 4.08-3.80 (m, 6H, H-4, H-3, 2×OCH$_2$); 2.03-1.92 (m, 2H, H-2/1, H-2/2); 1.45 (s, 3H, MeC); 1.44 (s, 3H, MeC)

EXAMPLE 7

[(4S,5R)-5-[2-(1,3-dioxolan-2-yl)acetyl]-2,2-dimethyl-1,3-dioxolan-4-yl]methyl benzoate; formula (VII); R$_7$=R$_8$=CH$_2$; R$_9$=R$_{10}$=CH$_3$; X=O; Y=[C(=O)]

A solution of 22.7 mL (0.31 mol) of DMSO and 10 mL of dichloromethane is cooled to −70° C., and 18.53 g (0.14 mol) of oxalyl chloride are slowly added dropwise under inert gas, in such a way that the temperature does not exceed −60° C. The reaction mixture is stirred at −70° C. for 50 minutes. Subsequently, 34.22 g (0.1 mol) of [(4S,5S)-5-[2-(1,3-dioxolan-2-yl)-1-hydroxyethyl]-2,2-dimethyl-1,3-dioxolan-4-yl]methyl benzoate (II) dissolved in 20 mL of dichloromethane are added dropwise, making sure that the temperature does not exceed −60° C. Subsequently, the reaction mixture is stirred at −70° C. for 50 min. Thereafter, 79.84 g (0.73 mol) of triethylamine are added dropwise and the mixture is stirred at −70° C. for a further 30 min. The reaction mixture is then warmed gradually to room temperature and 250 mL of H$_2$O and 200 mL of dichloromethane are added. The phases are separated and the aqueous phase is extracted once with 100 mL of dichloromethane. The combined organic phases are washed once with 100 mL of sulfuric acid (0.1% in H$_2$O), once with 100 mL of saturated NaHCO$_3$ solution (and once with 100 mL of saturated NaCl solution), dried over Na$_2$SO$_4$, filtered and concentrated by evaporation. 33.73 g (99%) of colorless oil are obtained.

$^1$H NMR (500 MHz; CDCl$_3$): δ (ppm)=8.02 (d, J=7.2 Hz, 2H, Ar); 7.53 (t, J=7.2 Hz, 1H, Ar); 7.41 (t, J=7.6 Hz, 2H, Ar); 5.30 (t, J=5.2 Hz, 1H, H-1); 4.62 (dd, J1=11.6 Hz, J2=3.1 Hz, 1H, H-6/1); 4.37 (m, 3H, H-4, H-5, H-6/2); 3.94 (m, 2H, OCH$_2$); 3.83 (m, 2H, OCH$_2$); 3.04 (d, J=5.3, 2H, H-2/1, H-2/2); 1.44 (s, 3H, MeC); 1.41 (s, 3H, MeC)

EXAMPLE 8

[(4S,5S)-5-[(E)-C-(1,3-dioxolan-2-ylmethyl)-N-hydroxy-carbonimidoyl]-2,2-dimethyl-1,3-dioxolan-4-yl]methyl benzoate; formula (VII); $R_7=R_8=CH_2$; $R_9=R_{10}=CH_3$; X=O; Y=[C(=N)—OH]

To a solution of 24.52 g (0.07 mol) of [(4S,5R)-5-[2-(1,3-dioxolan-2-yl)acetyl]-2,2-dimethyl-1,3-dioxolan-4-yl]methyl benzoate (II) in 80 mL of pyridine are added 31.58 g (0.45 mol) of hydroxylamine hydrochloride ($NH_2OH.HCl$). This is followed by stirring under inert gas at 55° C. for 13 h. The pyridine is removed by means of a rotary evaporator and the residue is then dried under high vacuum. Thereafter, 250 mL of $H_2O$ and 250 mL of ethyl acetate are added and the phases are separated. The aqueous phase is extracted four times with ethyl acetate (4×50 mL). The combined organic phases are washed with saturated NaCl solution and dried over sodium sulfate, filtered and concentrated by evaporation. 24.24 g (94%) of yellow oil are obtained.

$^1$H NMR (500 MHz; $CDCl_3$): δ (ppm)=8.05 (d, J=7.2 Hz, 2H, Ar); 7.56 (t, J=7.2 Hz, 1H, Ar); 7.43 (t, J=7.7 Hz, 2H, Ar); 5.31 (t, J=4.7 Hz, 1H, H-1); 4.58 (m, 3H, H-4, H-5, H-6/1); 4.40 (m, 1H, H-6/2); 3.98 (m, 2H, $OCH_2$); 3.84 (m, 2H, $OCH_2$); 2.78 (m, 2H, H-2/1, H-2/2); 1.46 (s, 6H, $Me_2C$)

EXAMPLE 9

2-(1,3-dioxolan-2-yl)-1-[(4S,5S)-5-(hydroxymethyl)-2,2-dimethyl-1,3-dioxolan-4-yl]ethanone oxime; formula (II); $R_7=R_8=CH_2$; $R_9=R_{10}=CH_3$; $R_4$=H; X=O; Y=[C(=N)—OH]

To a solution of 16.0 g (43.79 mmol) of [(4S,5S)-5-[(E)-C-(1,3-dioxolan-2-ylmethyl)-N-hydroxycarbon-imidoyl]-2,2-dimethyl-1,3-dioxolan-4-yl]methyl benzoate (II) in 340 mL of THF/$H_2O$ (1:1) are added dropwise 32 mL of 2N NaOH (63.96 mmol), and the mixture is stirred at 60° C. for 18 h. After cooling to room temperature, 200 mL of MTBE are added, the phases are separated and the aqueous phase is extracted four times with MTBE. The combined organic phases are washed with saturated NaCl solution and dried over sodium sulfate, filtered and concentrated. 9.31 g (81%) of yellow oil are obtained.

$^1$H NMR (500 MHz; $CDCl_3$): δ (ppm)=9.07 (s, 1H, OH); 5.35 (t, J=5.3 Hz, 1H, H-1); 4.45 (d, J=8.5 Hz, 1H, H-4); 4.27 (m, 1H, H-5); 3.97 (m, 2H, $OCH_2$); 3.78 (m, 3H, $OCH_2$, H-6); 3.09 (s, 1H, OH); 2.74 (m, 2H, H-2/1, H-2/2); 1.43 (s, 6H, $Me_2C$)

EXAMPLE 10

2-(1,3-dioxolan-2-yl)-1-[(4S,5S)-5-[2-[2-[2-[2-(2-methoxyethoxy)ethoxy]ethoxy]ethoxy]ethoxymethyl]-2,2-dimethyl-1,3-dioxolan-4-yl]ethanone oxime; formula (II); $R_7=R_8=CH_2$; $R_9=R_{10}=CH_3$; $R_4$=[(—$CH_2$—$CH_2$—O)$_5$—$CH_3$]; X=O; Y=[C(=N)—OH]

To a solution of 7.8 g (29.9 mmol) of 2-(1,3-dioxolan-2-yl)-1-[(4S,5S)-5-(hydroxymethyl)-2,2-dimethyl-1,3-dioxolan-4-yl]ethanone oxime (II) in 150 mL of THF are added 2.26 g of sodium hydride (95%) (89.8 mmol) in portions and the mixture is stirred at room temperature under inert gas for 1.5 h. Subsequently, 24.3 g (60 mmol) of 2-[2-[2-[2-(2-methoxyethoxy)ethoxy]-ethoxy]ethoxy]ethyl 4-methylbenzenesulfonate dissolved in 50 mL of THF are added dropwise and the mixture is stirred at 60° C. for a further 5 h. The reaction is then quenched with saturated $NH_4Cl$ solution. Thereafter, 300 mL of DCM are added, the phases are separated and the aqueous phase is extracted four times with DCM. The combined organic phases are dried over $Na_2SO_4$, filtered and concentrated by evaporation. The resulting oil is purified by chromatography (eluent: toluene/acetone 2:1→1:1, v/v). 12.4 g (84%) of yellow oil are obtained.

$^1$H NMR (500 MHz; $CDCl_3$): δ (ppm)=5.32 (t, J=5.3 Hz, 1H, H-1); 4.38 (m, 1H, H-5); 4.28 (d, J=8.2 Hz, 1H, H-4); 3.95 (m, 2H, $OCH_2$); 3.82 (m, 2H, $OCH_2$); 3.64 (m, 18H, $CH_2O$); 3.52 (m, 4H, H-6, $MeOCH_2$); 3.35 (s, 3H, OMe); 2.73 (d, J=5.7 Hz, 2H, H-2/1, H-2/2); 1.42 (s, 3H, MeC); 1.40 (s, 3H, MeC)

EXAMPLE 11

(1S)-2-(1,3-dioxolan-2-yl)-1-[(4S,5S)-5-[2-[2-[2-[2-(2-methoxyethoxy)ethoxy]ethoxy]ethoxy]ethoxymethyl]-2,2-dimethyl-1,3-dioxolan-4-yl]ethanamine; formula (II); $R_7=R_8=CH_2$; $R_9=R_{10}=CH_3$; $R_4$= [(—$CH_2$—$CH_2$—O)$_5$—$CH_3$]; X=O; Y=[CH—$NH_2$]; Y=[CH—$NR_5R_6$], $R_5=R_6$=H A solution of 12.4 g (25 mmol) of 2-(1,3-dioxolan-2-yl)-1-[(4S,5S)-5-[2-[2-[2-[2-(2-methoxyethoxyl)ethoxy]-ethoxy]ethoxy]ethoxymethyl]-2,2-dimethyl-1,3-dioxolan-4-yl]ethanone oxime (II) in 125 mL of THF under inert gas is cooled to 0° C. Connecting, 3.1 g (82.2 mmol) of lithium aluminum hydride ($LiAlH_4$) are added gradually while stirring. This is followed by stirring at RT for 4 h. The reaction is quenched with NaOH solution (5M), 100 mL of EtOAc are added and the mixture is stirred for 10 min. The reaction mixture is then filtered and the phases are separated. The combined organic phases are washed with saturated NaCl solution and dried over sodium sulfate, filtered and concentrated by evaporation. 9.8 g (81%) of yellow oil (mixture of the diastereomers 57:43 of 3') are obtained.

$^1$H NMR (200 MHz; $CDCl_3$): δ (ppm)=5.01 (t, J=4.73 Hz, 1H, H-1); 4.20-3.77 (m, 7H, H-4, H-5, H-6, 2×$OCH_2$); 3.64 (m, 18H, $CH_2O$); 3.53 (m, 2H, $MeOCH_2$); 3.35 (s, 3H, OMe); 3.19-3.00 (m, 1H, H-3); 2.24-1.56 (m, 2H, H-2); 1.38 (s, 3H, MeC); 1.37 (s, 3H, MeC)

EXAMPLE 12

N-[2-(1,3-dioxolan-2-yl)-1-[(4S,5S)-5-[2-[2-[2-[2-(2-methoxyethoxy)ethoxy]ethoxy]ethoxy]ethoxymethyl]-2,2-dimethyl-1,3-dioxolan-4-yl]ethyl]-2,2,2-trifluoroacetamide; formula (II); $R_7=R_8=CH_2$; $R_9=R_{10}=CH_3$; $R_4$=[(—$CH_2$—$CH_2$—O)$_5$—$CH_3$]; X=O; Y=[CH—$NR_5R_6$], $R_5$=H, $R_6$=[C(=O)$CF_3$]

To a solution of 9.8 g (20.3 mmol) of (1S)-2-(1,3-dioxolan-2-yl)-1-[(4S,5S)-5-[2-[2-[2-[2-(2-methoxyethoxy)ethoxy]ethoxy]ethoxy]ethoxymethyl]-2,2-dimethyl-1,3-dioxolan-4-yl]ethanamine (II) in 196 mL of DCM and 9.6 mL of pyridine is added 0.05 g (0.4 mmol) of 4-(dimethylamino)pyridine. The reaction mixture is cooled to −17° C. and 6.41 g (30.5 mmol) of trifluoroacetic anhydride are added dropwise. Thereafter, the mixture is warmed to room temperature within 4 h while stirring, all the solvents are concentrated by evaporation and the residue is taken up in dichloromethane. The organic phase is washed with semi-saturated $NaHCO_3$ solution and saturated NaCl solution, dried over sodium sulfate, filtered and concentrated by evaporation. The resulting oil is purified by chromatography (eluent: petroleum ether/acetone 2:1, v/v). 9.5 g (80%) of yellow oil (mixture of the diastereomers 57:43 of 3') are obtained.

$^1$H NMR (diastereomer 1), (500 MHz; CDCl$_3$): δ (ppm)=7.65 (d, J=8.85 Hz, 1H, NH); 4.99 (t, J=4.6 Hz, 1H, H-1); 4.30 (m, 1H, H-3); 3.92 (m, 7H, H-4, H-5, H-6, 2×OCH$_2$); 3.62 (m, 18H, CH$_2$O); 3.52 (m, 2H, MeOCH$_2$); 3.35 (s, 3H, OMe); 2.04 (m, 2H, H-2); 1.38 (s, 3H, MeC); 1.37 (s, 3H, MeC)

$^1$H NMR (diastereomer 2), (500 MHz; CDCl$_3$): δ (ppm)=6.95 (d, J=9.15 Hz, 1H, NH); 4.96 (t, J=4.4 Hz, 1H, H-1); 4.40 (m, 1H, H-3); 3.92 (m, 7H, H-4, H-5, H-6, 2×OCH$_2$); 3.62 (m, 18H, CH$_2$O); 3.52 (m, 2H, MeOCH$_2$); 3.35 (s, 3H, OMe); 2.04 (m, 2H, H-2); 1.38 (s, 3H, MeC); 1.1.37 (s, 3H, MeC)

EXAMPLE 13

(2S,5S)-2-tert-butyl-5-[2-(tert-butyl(dimethyl)silyl)-oxyethyl]-1,3-dioxolan-4-one; formula (IX)

40 g of 2-[(2S,4S)-2-tert-butyl-5-oxo-1,3-dioxolan-4-yl] acetic acid are dissolved in 300 mL of THF under an argon atmosphere and cooled to 0° C. 238 mL of BH$_3$.THF complex (1M in THF) are added gradually within one hour, in such a way that the temperature does not rise above 5° C. On completion of addition of the reagent, the reaction mixture is stirred at 0° C. for 20 min, warmed to room temperature and stirred for 3.5 hours. The reaction mixture is partitioned between saturated NH$_4$Cl solution and EtOAc. The phases are separated and the aqueous phase is extracted with EtOAc. The combined organic phases are washed with 5% aqueous NaHCO$_3$ solution and saturated sodium chloride solution, dried over Na$_2$SO$_4$, filtered and concentrated by evaporation under reduced pressure. 32 g of intermediate are obtained, which can be used directly in the next stage without further purification.

43 g of TBDMSCl in 500 mL of DCM are admixed with 45.1 g of pyridine. The solution is stirred for 10 min, then the intermediate, dissolved in 100 mL of DCM, is added. The reaction mixture is stirred at room temperature for 16 hours and then poured onto water. The phases are separated, the organic phase is washed with 5% aqueous NaHCO$_3$ solution, dried over Na$_2$SO$_4$, filtered and concentrated by evaporation under reduced pressure. The crude product is purified by means of flash chromatography over silica gel with toluene as eluent. 52.3 g of (2S,5S)-2-tert-butyl-5-[2-(tert-butyl(dimethyl)silyl)oxyethyl]-1,3-dioxolan-4-one are obtained as a colorless oil.

$^1$H NMR (500 MHz; CDCl$_3$): δ (ppm)=5.15 (s, 1H, H-5); 4.43 (dd, 1H, 3.8 Hz, 8.5 Hz, H-3); 3.80 (m, 2H, H-1); 2.12 (m, 1H, H-2/1); 1.86 (m, 1H, H-2/2); 0.97 (s, 9H, H-tBuCH$_3$); 0.89 (s, 9H, H-SitBuCH$_3$); 0.06 (s, 6H, H—SiCH$_3$).

EXAMPLE 14 (ALKYLATION REACTION)

(2S,5S)-2-tert-butyl-5-[2-(tert-butyl(dimethyl)silyl)-oxyethyl]-5-[(1,4,9,10-tetramethoxy-2-anthryl) methyl]-1,3-dioxolan-4-one; formula (X); R$_1$=H To a solution of 18 g of KHMDS in 680 mL of anhydrous THF is added dropwise, under an argon atmosphere at −76° C., a solution of 25.6 g of (2S,5S)-2-tert-butyl-5-[2-(tert-butyl(dimethyl)silyl)oxyethyl]-1,3-dioxolan-4-one in 30 mL of THF, in such a way that the temperature does not rise above −72° C. The reaction mixture is stirred at −76° C. for 50 minutes. A solution of 22 g of 2-(bromomethyl)-1,4,9,10-tetramethoxyanthracene in 40 mL of THF is added dropwise at −75° C. The mixture is then stirred at this temperature for 20 min. The reaction mixture is partitioned between 1N HCl and EtOAc. The aqueous phase is extracted with EtOAc and the combined organic phases are dried over Na$_2$SO$_4$, filtered and concentrated by evaporation under reduced pressure. The crude product is digested in a mixture of 50 mL of MTBE and 200 mL of PE, filtered and washed with PE. 23.4 g of (2S,5S)-2-tert-butyl-5-[2-(tert-butyl(dimethyl)silyl)oxyethyl]-5-[(1,4,9,10-tetramethoxy-2-anthryl)methyl-1,3-dioxolan-4-one are obtained as a yellow solid. The filtrate is concentrated by evaporation under reduced pressure and separated by means of column chromatography (silica gel, toluene/EtOAc 30/1). In this way, a further 7.4 g of (2S,5S)-2-tert-butyl-5-[2-(tert-butyl(dimethyl)-silyl)oxyethyl]-5-[(1,4,9,10-tetramethoxy-2-anthryl)-methyl-1,3-dioxolan-4-one are obtained.

$^1$H NMR (500 MHz; CDCl$_3$): δ (ppm)=8.35 (m, 2H, H-5 and H-8); 7.52 (m, 2H, H-6 and H-7); 6.64 (s, 1H, H-3); 4.84 (s, 1H, H-acetal); 4.02 (s, 3H, OCH$_3$-4); 4.00 (s, 3H, OCH$_3$-10); 3.95 (s, 3H, OCH$_3$-9); 3.83 (m, 2H, H-4'); 3.75 (s, 3H, OCH$_3$-1); 3.44 (d, 1H, J=13.9 Hz, H-1'/1); 3.18 (d, 1H, J=13.9 Hz, H-1'/2); 2.17 (m, 2H, H-3'); 0.89 (s, 9H, H-tBuCH$_3$); 0.88 (s, 9H, H-SitBuCH$_3$); 0.05 (s, 3H, H—SiCH$_3$); 0.04 (s, 3H, H—SiCH$_3$).

EXAMPLE 15

(3S)-5-(tert-Butyl(dimethyl)silyl)oxy-3-hydroxy-3-[(1,4,9,10-tetramethoxy-2-anthryl)methyl]pentan-2-one; formula (XI); R$_4$=H To a solution of 62 g of (2S,5S)-2-tert-butyl-5-[2-(tert-butyl(dimethyl)silyl)oxyethyl]-5-[(1,4,9,10-tetramethoxy-2-anthryl)methyl]-1,3-dioxolan-4-one in 700 mL of anhydrous THF are added dropwise, under an argon atmosphere at −78° C., 164 mL of MeLi (1.6 M in Et$_2$O), in such a way that the temperature does not rise above −71° C. The reaction mixture is stirred at −75° C. for 1.5 hours and then partitioned between saturated NH$_4$Cl solution and EtOAc. The aqueous phase is extracted with EtOAc. The combined organic phases are dried over Na$_2$SO$_4$, filtered and concentrated by evaporation under reduced pressure. The crude product is purified by means of column chromatography (silica gel, toluene/EtOAc, 10/1). 54.2 g of (3S)-5-(tert-butyl-(dimethyl)silyl)oxy-3-hydroxy-3-[(1,4,9,10-tetramethoxy-2-anthryl)methyl]pentan-2-one are obtained as a yellow foam.

$^1$H NMR (500 MHz; CDCl$_3$): δ (ppm)=16.67 (m, 2H, H-5 and H-8); 7.51 (m, 2H, H-6 and H-7); 6.70 (s, 1H, H-3); 4.01 (s, 3H, OCH$_3$-4); 3.98 (s, 3H, OCH$_3$-10); 3.92 (s, 3H, OCH$_3$-9); 3.82 (td, 1H, J=4.1 Hz, 9.2 Hz, H-4'/1); 3.77 (s, 3H, OCH$_3$-1); 3.70 (dt, 1H, J=5.1 Hz, 10.4 Hz, H-4'/2); 3.27 (d, 1H, J=12.9 Hz, H-1'/1); 3.12 (d, 1H, J=12.9 Hz, H-1'/2); 2.39 (m, 1H, H-3'/1); 2.33 (s, 3H, CH$_3$); 1.96 (dt, 1H, J=4.4 Hz, 14.2 Hz, H-3'/2); 0.86 (s, 9H, H-SitBuCH$_3$); 0.02 (s, 3H, H—SiCH$_3$); 0.01 (s, 3H, H—SiCH$_3$).

EXAMPLE 16 a. Reduction of the Keto Group (2S,3S)-5-(tert-Butyl(dimethyl)silyl)oxy-3-[(1,4,9, 10-tetramethoxy-2-anthryl)methyl]pentane-2,3-diol To a solution of 33.8 g of (3S)-5-(tert-butyl-(dimethyl) silyl)oxy-3-hydroxy-3-[(1,4,9,10-tetramethoxy-2-anthryl)

methyl]pentan-2-one in 340 mL of EtOH are added, under an argon atmosphere, 2.36 g of NaBH$_4$. The reaction mixture is stirred at RT for one hour and then quenched with saturated sodium chloride solution and EtOAc. The aqueous phase is extracted with EtOAc. The combined organic phases are dried over Na$_2$SO$_4$, filtered and concentrated by evaporation under reduced pressure. The crude product is purified by means of flash chromatography (silica gel, toluene/EtOAc=5:1). 30.70 g (2S,3S)-5-(tert-butyl(dimethyl)silyl)oxy-3-[(1,4,9,10-tetramethoxy-2-anthryl)methyl]pentane-2,3-diol are obtained as a yellow foam.

b. Ketalization tert-Butyldimethyl-[2-[(4S,5S)-2,2,5-trimethyl-4-[(1,4,9,10-tetramethoxy-2-anthryl)methyl]-1,3-dioxolan-4-yl]ethoxy]silane; formula (XII), R$_1$=H To a solution of 5.26 g of the alcoholic intermediate in 100 mL of dry acetone are added, under an argon atmosphere, 2.6 mL of dimethoxypropane followed by 0.09 g of pTsOH. The reaction mixture is stirred at RT for 1.5 hours and then partitioned between saturated NaHCO$_3$ solution and EtOAc. The phases are separated: the aqueous phase is extracted with EtOAc. The combined organic phases are dried over Na$_2$SO$_4$, filtered and concentrated by evaporation under reduced pressure. The crude product is purified by means of flash chromatography (silica gel, toluene/EtOAc, 40/1). 4.66 g of tert-butyldimethyl-[2-[(4S,5S)-2,2,5-trimethyl-4-[(1,4,9,10-tetramethoxy-2-anthryl)methyl]-1,3-dioxolan-4-yl]ethoxy]silane are obtained as a yellow foam.

$^1$H NMR (500 MHz; CDCl$_3$): δ (ppm)=8.35 (m, 2H, H-5 and H-8); 7.50 (m, 2H, H-6 and H-7); 6.97 (s, 1H, H-3); 4.54 (q, 1H, J=6.3 Hz, H-5'); 4.02 (s, 3H, OCH$_3$-4); 3.98 (s, 3H, OCH$_3$-10); 3.92 (s, 3H, OCH$_3$-9); 3.73 (s, 3H, OCH$_3$-1); 3.69 (m, 2H, H-4'); 3.19 (d, 1H, J=13.6 Hz, H-1'/1); 2.75 (d, 1H, J=13.6 Hz, H-1'/2); 1.91 (m, 1H, H-3'/1); 1.77 (m, 1H, H-3'/2); 1.74 (s, 3H, H-acetonide); 1.45 (d, 3H, J=6.3 Hz, CH$_3$); 1.44 (s, 3H, H-acetonide); 0.86 (s, 9H, H-SitBuCH$_3$); 0.01 (s, 6H, H—SiCH$_3$).

EXAMPLE 17 a. Detachment of the TBDMS Group

2-[(4S,5S)-2,2,5-Trimethyl-4-[(1,4,9,10-tetramethoxy-2-anthryl)methyl]-1,3-dioxolan-4-yl]ethanol To a solution of 4.57 g of tert-butyldimethyl-[2-[(4S,5S)-2,2,5-trimethyl-4-[(1,4,9,10-tetramethoxy-2-anthryl)methyl]-1,3-dioxolan-4-yl]ethoxy]silane in 90 mL of anhydrous THF are added at RT, under an argon atmosphere, 19.5 mL of TBAF (1M in THF). The reaction mixture is stirred at RT for 1 hour. The reaction mixture is partitioned between saturated NaHCO$_3$ solution and EtOAc. The aqueous phase is extracted with EtOAc. The combined organic phases are dried over Na$_2$SO$_4$, filtered and concentrated by evaporation under reduced pressure. 603 g of 2-[(4S,5S)-2,2,5-trimethyl-4-[(1,4,9,10-tetramethoxy-2-anthryl)methyl]-1,3-dioxolan-4-yl]ethanol are obtained as a yellow foam.

$^1$H NMR (500 MHz; CDCl$_3$): δ (ppm)=8.35 (m, 2H, H-5 and H-8); 7.51 (m, 2H, H-6 and H-7); 6.93 (s, 1H, H-3); 4.37 (q, 1H, J=6.3 Hz, H-5'); 4.02 (s, 3H, OCH$_3$-4); 4.00 (s, 3H, OCH$_3$-10); 3.93 (s, 3H, OCH$_3$-9); 3.81 (m, 1H, H-4'/1); 3.78 (s, 3H, OCH$_3$-1); 3.66 (m, 1H, H-4'/2); 3.22 (d, 1H, J=13.6 Hz, H-1'/1; 2.81 (brs, 1H, OH-4'); 2.75 (d, 1H, J=13.6 Hz, H-1'/2); 1.88 (m, 2H, H-3'); 1.75 (s, 3H, H-acetonide); 1.48 (d, 3H, J=6.3 Hz, CH$_3$); 1.47 (s, 3H, H-acetonide).

b. Oxidation of the Primary Alcohol to the Aldehyde

2-[(4S,5S)-2,2,5-Trimethyl-4-[(1,4,9,10-tetramethoxy-2-anthryl)methyl]-1,3-dioxolan-4-yl]acetaldehyde; formula (XIII); R$_1$=H Added dropwise to a solution of 0.99 mL of DMSO in 55 mL of DCM at −70° C. is 0.61 mL of oxalyl chloride under an argon atmosphere. The mixture is stirred at −70° C. for 1 hour. Subsequently, 2.19 g of 2-[(4S,5S)-2,2,5-trimethyl-4-[(1,4,9,10-tetramethoxy-2-anthryl)-methyl]-1,3-dioxolan-4-yl]ethanol in 4 mL of DCM are added gradually at −70° C. The reaction mixture is stirred for 1 hour. 4.27 mL of Et$_3$N are added at the same temperature. Stirring is continued while gradually warming to 0° C. for another 1 hour. The reaction mixture is partitioned between saturated sodium chloride solution and EtOAc. The organic phase is washed successively with saturated NH$_4$Cl solution, saturated NaHCO$_3$ solution and saturated sodium chloride solution, dried over Na$_2$SO$_4$, filtered and concentrated under reduced pressure. 2.1 g of 2-[(4S,5S)-2,2,5-trimethyl-4-[(1,4,9,10-tetramethoxy-2-anthryl)methyl]-1,3-dioxolan-4-yl] acetaldehyde are obtained as a yellow foam.

$^1$H NMR (500 MHz; CDCl$_3$): δ (ppm)=9.65 (dd, 1H, J=1.3 Hz, 2.2 Hz, H-4'); 8.34 (m, 2H, H-5 and H-8); 7.51 (m, 2H, H-6 and H-7); 6.81 (s, 1H, H-3); 4.28 (q, 1H, J=6.3 Hz, H-5'); 4.03 (s, 3H, OCH$_3$-4); 3.99 (s, 3H, OCH$_3$-10); 3.91 (s, 3H, OCH$_3$-9); 3.70 (s, 3H, OCH$_3$-1); 3.23 (d, 1H, J=13.6 Hz, H-1'/1); 2.77 (dd, 1H, J=2.2 Hz, 16.4 Hz, H-3'/1); 2.73 (d, 1H, J=13.6 Hz, H-1'/2); 2.62 (dd, 1H, J=1.3 Hz, 16.34 Hz, H-3'/2); 1.74 (s, 3H, H-acetonide); 1.55 (s, 3H, J=6.3 Hz, CH$_3$); 1.40 (s, 3H, H-acetonide).

c. Oxidative Demethylation

2-[(4S,5S)-4-[(1,4-dimethoxy-9,10-dioxo-2-anthryl)-methyl]-2,2,5-trimethyl-1,3-dioxolan-4-yl]acetaldehyde; formula (XIV), R$_1$=H To a solution of 2.08 g of 2-[(4S,5S)-2,2,5-trimethyl-4-[(1,4,9,10-tetramethoxy-2-anthryl)methyl]-1,3-dioxolan-4-yl]acetaldehyde in 60 mL of CH$_3$CN is added, at 2° C., a solution of 7.3 g of CAN in 130 mL of water. After stirring for 30 min, the reaction mixture is diluted with 80 mL of water. The aqueous phase is extracted with EtOAc. The combined organic phases are dried and concentrated by evaporation. The resulting mixture is separated by chromatography (eluent: toluene/EtOAc 6:1). 1.91 g of 2-[(4S,5S)-4-[(1,4-dimethoxy-9,10-dioxo-2-anthryl)methyl]-2,2,5-trimethyl-1,3-dioxolan-4-yl]acetaldehyde are obtained as a yellow solid.

$^1$H NMR (500 MHz; CDCl$_3$): δ (ppm)=9.62 (dd, 1H, J=1.6 Hz, 2.5 Hz, H-4'); 8.16 (m, 2H, H-5 and H-8); 7.71 (m, 2H, H-6 and H-7); 7.45 (s, 1H, H-3); 4.25 (q, 1H, J=6.3 Hz, H-5'); 4.00 (s, 3H, OCH$_3$-4); 3.81 (s, 3H, OCH$_3$-1); 3.18 (d, 1H, J=12.9 Hz, H-1'/1); 2.66 (d, 1H, J=12.9 Hz, H-1'/2); 2.65 (dd, 1H, J=2.5 Hz and 16.4 Hz, H-3'/1); 2.48 (dd, 1H, J=1.6 Hz, 16.4 Hz, H-3'/2); 1.64 (s, 3H, H-acetonide); 1.50 (d, 3H, J=6.3 Hz, CH$_3$); 1.34 (s, 3H, H-acetonide).

EXAMPLE 18

2-[[(2S,3S)-3,5-dihydroxy-2-methyltetrahydrofuran-3-yl]methyl]-1,4-dihydroxyanthracene-9,10-dione; formula (XV); R$_1$=H To a solution of 1 g of 2-[(4S,5S)-4-[(1,4-dimethoxy-9,10-dioxo-2-anthryl)methyl]-2,2,5-trimethyl-1,3-dioxolan-4-yl]acetaldehyde in 55 mL of DCM are added dropwise at 2° C., under an argon atmosphere, 13.7 mL of BCl$_3$ (1M in DCM). The reaction mixture is stirred for 40 min, and 0.5 N NaOH and DCM are added. The phases are separated; the organic phase is washed with 0.5 N NaOH. The combined aqueous phases are acidified to pH=6 at 0° C. with 1 N HCl and extracted with DCM. The combined organic phases are dried and concentrated by evaporation. 0.79 g of 2-[[(2S,3S)-3,5-dihydroxy-2-methyltetrahydrofuran-3-yl]methyl]-1,4-dihydroxyanthracene-9,10-dione is obtained as a red solid.

$^1$H NMR (500 MHz; CDCl$_3$): δ (ppm)=13.66 (s, 1H, OH-1); 12.87 (s, 1H, OH-4); 8.36 (m, 2H, H-5 and H-8); 7.85 (m, 2H, H-6 and H-7); 7.29 (s, 1H, H-3); 5.38 (m, 1H, H-4'); 4.01 (q, 1H, J=6.3 Hz, H-6'); 3.52 (d, 1H, J=7.3 Hz, OH-4'); 3.39 (s, 1H, OH-2'); 3.07 (d, 1H, J=13.6 Hz, H-1'/1); 2.90 (d, 1H, J=13.6 Hz, H-1'/2); 2.21 (dd, 1H, J=5.1, 13.3 Hz, H-3'/1; 1.99 (d, 1H, J=13.3 Hz, H-3'/2); 1.34 (d, 3H, J=6.3 Hz, CH$_3$).

EXAMPLE 19 a. Intramolecular Ring Closure as Per Marschalk (7R,9S)-6,7,9,11-tetrahydroxy-9-[(1S)-1-hydroxyethyl]-8,10-dihydro-7H-tetracene-5,12-dione; formula (XVI); R$_1$, R$_{13}$=H; R$_{12}$=OH and (7S,9S)-6,7,9,11-tetrahydroxy-9-[(1S)-1-hydroxyethyl]-8,10-dihydro-7H-tetracene-5,12-dione; formula (XVI); R$_1$, R$_{12}$=H; R$_{13}$=OH To a solution of 70 mg of 2-[[(2S,3S)-3,5-dihydroxy-2-methyltetrahydrofuran-3-yl]methyl]-1,4-dihydroxyanthracene-9,10-dione in 5 mL of THF and 5 mL of MeOH is added dropwise, under an argon atmosphere at −10° C., a solution of 38 mg of NaOH and 49 mg of Na$_2$S$_2$O$_4$ in 1.2 mL of water. After stirring for two hours, the reaction mixture is quenched by blowing air in for 30 min. The reaction mixture is admixed with 0.05 N HCl and EtOAc. The phases are separated; the aqueous phase is extracted with EtOAc. The combined organic phases are dried and concentrated by evaporation. The resulting mixture is separated by chromatography (eluent: toluene/isopropanol 30:1). 37 mg of a mixture of (7R,9S)-6,7,9,11-tetrahydroxy-9-[(1S)-1-hydroxyethyl]-8,10-dihydro-7H-tetracene-5,12-dione and (7S,9S)-6,7,9,11-tetrahydroxy-9-[(1S)-1-hydroxyethyl]-8,10-dihydro-7H-tetracene-5,12-dione are obtained as a red solid.

(7R,9S)-6,7,9,11-tetrahydroxy-9-[(1S)-1-hydroxyethyl]-8,10-dihydro-7H-tetracene-5,12-dione $^1$H NMR (500 MHz; CDCl$_3$): δ=13.60 (s, 1H, OH-6); 13.33 (s, 1H, OH-11); 8.23 (m, 2H, H-1 and H-4); 7.95 (m, 2H, H-2 and H-3); 5.17 (d, 1H, J=5.7 Hz, OH-7); 5.05 (m, 1H, H-7); 4.85 (d, 1H, J=5.7 Hz, OH-13); 4.45 (s, 1H, OH-9); 3.54 (q, 1H, J=6.3 Hz, H-13); 2.85 (d, 1H, J=18.3 Hz, H-10/1); 2.68 (d, 1H, J=18.3 Hz, H-10/2); 2.14 (m, 1H, H-8/1); 1.75 (m, 1H, H-8/2); 1.14 (d, 3H, J=6.3 Hz, CH$_3$).

(7S,9S)-6,7,9,11-tetrahydroxy-9-[(1S)-1-hydroxyethyl]-8,10-dihydro-7H-tetracene-5,12-dione $^1$H NMR (500 MHz; CDCl$_3$): δ=13.42 (s, 1H, OH-6); 13.30 (s, 1H, OH-11); 8.23 (m, 2H, H-1 and H-4); 7.95 (m, 2H, H-2 and H-3); 5.30 (d, 1H, J=7.9 Hz, OH-7); 5.14 (s, 1H, OH-9); 5.00 (m, 1H, H-7); 4.81 (d, 1H, J=5.7 Hz, OH-13); 3.54 (q, 1H, 6.3 Hz, H-13); 2.88 (d, 1H, J=18.3 Hz, H-10/1); 2.75 (d, 1H, J=18.3 Hz, H-10/2); 2.14 (m, 1H, H-8/1); 1.75 (m, 1H, H-8/2); 1.16 (d, 3H, J=6.3 Hz, CH$_3$).

b. Intramolecular Ring Closure as Per Marschalk (9R)-6,9,11-trihydroxy-9-[(1S)-1-hydroxyethyl]-8,10-dihydro-7H-tetracene-5,12-dione; formula (XVI); R$_1$, R$_{12}$, R$_{13}$=H To a solution of 0.79 g of 2-[[(2S,3S)-3,5-Dihydroxy-2-methyltetrahydrofuran-3-yl]methyl]-1,4-dihydroxyanthracene-9,10-dione in 31 mL of THF and 31 mL of MeOH is added dropwise, under an argon atmosphere at RT, a solution of 0.43 g of NaOH and 0.56 g of Na$_2$S$_2$O$_4$ in 5.3 mL of water. After stirring for 1.5 hours, the reaction mixture is quenched by blowing in air for 30 min. The reaction mixture is admixed with 0.05 N HCl and EtOAc. The phases are separated; the aqueous phase is extracted with EtOAc. The combined organic phases are dried and concentrated by evaporation. The resulting mixture is purified by digesting with toluene/EtOAc (1:1). 0.51 g of (9R)-6,9,11-trihydroxy-9-[(1S)-1-hydroxyethyl]-8,10-dihydro-7H-tetracene-5,12-dione is obtained as a red solid.

$^1$H NMR (500 MHz; CDCl$_3$): δ (ppm)=13.36 (s, 1H, OH-11); 13.35 (s, 1H, OH-6); 8.21 (m, 2H, H-1 and H-4); 7.94 (m, 2H, H-2 and H-3); 4.69 (d, 1H, J=6.3 Hz, OH-13); 4.28 (s, 1H, OH-9); 3.56 (m, 1H, H-13); 2.82 (d, 1H, J=18.3 Hz, H-7/1); 2.66 (m, 3H, H-7/2 and H-10); 1.88 (m, 1H, H-8/1); 1.51 (m, 1H, H-8/2); 1.14 (d, 3H, J=6.3 Hz, CH$_3$).

EXAMPLE 20 a: Oxidation of the Side Chain Hydroxyl Group (9R)-9-Acetyl-6,9,11-trihydroxy-8,10-dihydro-7H-tetracene-5,12-dione; formula (XVII); R$_1$=H To a solution of 0.8 g of (9R)-6,9,11-trihydroxy-9-[(1S)-1-hydroxyethyl]-8,10-dihydro-7H-tetracene-5,12-dione (0.80 g, 2.258 mmol) in 45 mL of DCM are added, at RT under an argon atmosphere, 1.58 g of Dess-Martin periodinane (97%). After stirring for 5 hours, the reaction mixture is admixed with saturated NaHCO$_3$ solution and EtOAc. The phases are separated; the aqueous phase is extracted with EtOAc. The combined organic phases are dried and concentrated by evaporation. The resulting mixture is separated by chromatography (eluent: DCM/EtOAc 7:1). 0.60 g of (9R)-9-acetyl-6,9,11-trihydroxy-8,10-dihydro-7H-tetracene-5,12-dione (1.694 mmol, 75%) is obtained as a red solid.

$^1$H NMR (500 MHz; CDCl$_3$): δ (ppm)=13.48 (s, 1H, OH-11); 13.47 (s, 1H, OH-6); 8.35 (m, 2H, H-1 and H-4); 7.83 (m, 2H, H-2 and H-3); 3.16 (m, 1H, H-7/1); 3.07 (d, 1H, J=18 Hz, H-10/1); 2.95 (m, 2H, H-10/2 and H-7/2); 2.39 (s, 3H, CH3); 2.00 (m, 2H, H-8).

b: Hydroxylation at C-7

(7S,9S)-9-acetyl-6,7,9,11-tetrahydroxy-8,10-dihydro-7H-tetracene-5,12-dione; formula (IV); R₁=R₂=H To a suspension of 130 mg of (9R)-9-acetyl-6,9,11-trihydroxy-8,10-dihydro-7H-tetracene-5,12-dione in 35 mL of CCl₄ are added successively 1 mL of water, 74 mg of NBS and 18 mg of AIBN. The reaction mixture is subsequently heated under reflux for 90 minutes. A further 33 mg of NBS are added and the reaction mixture is heated under reflux for a further 2 hours. The reaction mixture is cooled to 20° C. and diluted with 15 mL of 10% K₂CO₃ solution and 20 mL of THF. After stirring for 10 minutes, the aqueous phase is brought to pH=1 with 1 N HCl and extracted with DCM. The combined organic phases are dried, filtered and concentrated under reduced pressure. The crude product is purified by chromatography on silica gel with toluene/EtOAc (10/1), giving 35 mg of (9R)-9-acetyl-6,9,11-trihydroxy-8,10-dihydro-7H-tetracene-5,12-dione, 16 mg of (7R,9S)-9-acetyl-6,7,9,11-tetrahydroxy-8,10-dihydro-7H-tetracene-5,12-dione and 48 mg of (7S,9S)-9-acetyl-6,7,9,11-tetrahydroxy-8,10-dihydro-7H-tetracene-5,12-dione as a red solid.

(7S,9S)-9-acetyl-6,7,9,11-tetrahydroxy-8,10-dihydro-7H-tetracene-5,12-dione

¹H NMR (500 MHz; CDCl₃): δ (ppm)=13.53 (s, 1H, OH-6); 13.25 (s, 1H, OH-11); 8.31 (m, 2H, H-1 and H-4); 7.84 (m, 2H, H-2 and H-3); 5.29 (brs, 1H, H-7); 4.58 (s, 1H, OH-9); 3.86 (d, 1H, J=5.0 Hz, OH-7); 3.17 (dd, 1H, J=2.2 Hz, 18.6 Hz, H-10/1); 2.94 (d, 1H, J=18.6 Hz, H-10/2); 2.44 (s, 3H, CH₃); 2.35 (m, 1H, H-8/1); 2.17 (dd, 1H, J=5.1 Hz, 14.5 Hz, H-8/2).

(7R,9S)-9-acetyl-6,7,9,11-tetrahydroxy-8,10-dihydro-7H-tetracene-5,12-dione

¹H NMR (500 MHz; CDCl₃): δ (ppm)=13.93 (s, 1H, OH-6); 13.30 (s, 1H, OH-11); 8.35 (m, 2H, H-1 and H-4); 7.85 (m, 1H, H-2 and H-3); 5.40 (dd, 1H, J=7.9 Hz, 8.6 Hz, H-7); 4.28 (d, 1H, J=1.6 Hz, OH-7); 3.90 (s, 1H, OH-9); 3.10 (d, 1H, J=18.0 Hz, H-10/1); 2.94 (d, 1H, J=18.0 Hz, H-10/2); 2.41 (s, 3H, CH₃); 2.35 (m, 1H, H-8/1); 2.18 (dd, 1H, J=9.8 Hz, 13.0 Hz, H-8/2).

EXAMPLE 21

Epimerization of (7R,9S)-9-acetyl-6,7,9,11-tetrahydroxy-8,10-dihydro-7H-tetracene-5,12-dione 26 mg of (7R,9S)-9-acetyl-6,7,9,11-tetrahydroxy-8,10-dihydro-7H-tetracene-5,12-dione, which may be contaminated with (7S,9S)-9-acetyl-6,7,9,11-tetrahydroxy-8,10-dihydro-7H-tetracene-5,12-dione, are dissolved in 1.3 mL of TFA. After stirring at RT for two hours, the reaction mixture is admixed with water and extracted with DCM. The combined organic phases are dried and concentrated by evaporation. The crude product is dissolved in 1 mL of acetone. Thereafter, saturated NaHCO₃ solution is added. After stirring for 10 min, the mixture is extracted with DCM. The combined organic phases are dried and concentrated by evaporation. The resulting product is purified by chromatography (eluent: toluene/EtOAc 10:1). 15 mg of (7S,9S)-9-acetyl-6,7,9,11-tetrahydroxy-8,10-dihydro-7H-tetracene-5,12-dione are obtained as a red solid.

¹H NMR (500 MHz; CDCl₃): δ (ppm)=13.53 (s, 1H, OH-6); 13.25 (s, 1H, OH-11); 8.31 (m, 2H, H-1 and H-4); 7.84 (m, 2H, H-2 and H-3); 5.29 (brs, 1H, H-7); 4.58 (s, 1H, OH-9); 3.86 (d, 1H, J=5.0 Hz, OH-7); 3.17 (dd, 1H, J=2.2 Hz, 18.6 Hz, H-10/1); 2.94 (d, 1H, J=18.6 Hz, H-10/2); 2.44 (s, 3H, CH₃); 2.35 (m, 1H, H-8/1); 2.17 (dd, 1H, J=5.1 Hz, 14.5 Hz, H-8/2).

The invention further relates to the following items of subject matter/compounds and uses:

1'. A compound of the general formula (I)

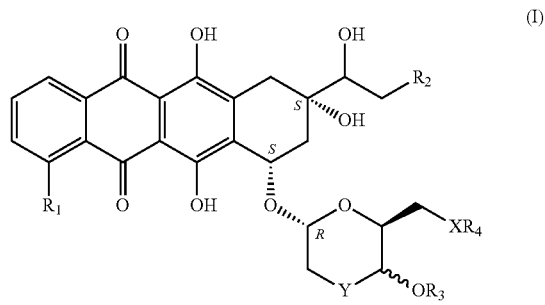

in which $R_1$ is a hydrogen atom or a hydroxyl or methoxy group; $R_2$ is a hydrogen atom or a hydroxyl group; $R_3$ is hydrogen or a suitable hydroxyl protecting group and the wavy line in each case means both possible configurations of —$OR_3$ in relation to the base structure; Y=[C(=O)], [C(=N)—OH] or [CH—OH], [CH—NR₅R₆] in both possible stereoisomeric arrangements, where $R_5$ and $R_6$ are the same or different and are each a hydrogen atom, or a suitable amino protecting group as known in the prior art, for instance from "Protective Groups in Organic Synthesis" (Greene, Wuts) 4th edition, John Wiley & Sons, Inc., pages 696 to 927, especially a trifluoroacetyl, unbranched or branched lower alkyl, where "lower alkyl" means a carbon number from 1 to 4, or an alkylene chain (—CH₂—CZ₂—CZ₂—CH₂—, —CH₂—CZ₂—CZ₂—CZ₂—CH₂—, —CH₂—O—CZ₂—CH₂—, —CH₂—O—CZ₂—CZ₂—CH₂—, —CH₂—CZ₂—O—CZ₂—CH₂—) where Z is defined as hydrogen, lower alkyl or lower alkoxy in any combination; in which X=O, S or NR; where R=hydrogen or lower alkyl; $R_4$ is an unbranched or branched alkyl or heteroalkyl chain having a chain length of 1 to 19 elements, where a maximum of 6 heteroatoms (O, N, S) in any combination are separated from one another by at least two carbon atoms.

2'. A compound of the general formula (I) in which X=O and $R_1$, $R_2$, $R_3$, $R_4$ and Y are each as defined in item 1'.

3'. A compound of the general formula (I) in which X=NR and $R_1$, $R_2$, $R_3$, $R_4$ and Y are each as defined in item 1'.

4'. A compound of the general formula (I) in which X=S and $R_1$, $R_2$, $R_3$, $R_4$ and Y are each as defined in item 1'.

5'. A compound as claimed in items 1' to 4' in which $R_4$ contains at least one ethylene glycol unit (—O—CH₂—CH₂—O—).

6'. A process for preparing compounds of the general formula (I) according to items 1' to 5', characterized in that an open-chain sugar compound of the general formula (II)

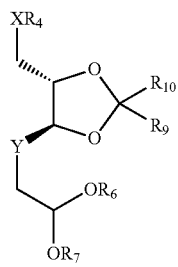
(II)

in which $R_7$ and $R_8$ are the same and are each alkyl or alkylene having 2 to 3 carbon atoms; $R_9$ and $R_{10}$ are each an alkyl group having 1 to 3 carbon atoms; X and Y are each as defined in formula (I) of item 1'; $R_4$ is hydrogen or a suitable hydroxyl protecting group as known in the prior art, for instance from "Protective Groups in Organic Synthesis" (Greene, Wuts) 4th edition, John Wiley & Sons, Inc., pages 16 to 288, especially a benzoyl group, or is as defined for $R_4$ in formula (I), is cyclized to give a sugar compound of the general formula (III)

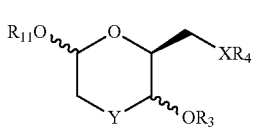
(III)

in which X, Y and $R_4$ are each as defined in formula (II), $R_3$ and $R_{11}$ are each an activating group known for glycosylation [C(=O)PhNO$_2$, OTFA] and the wavy lines in each case mean both possible configurations of —OR$_3$ and —OR$_{11}$ in relation to the base structure, and is reacted with an anthraquinone-derived aglycone of the general formula (IV)

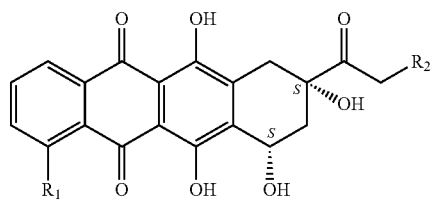
(IV)

in which $R_1$ and $R_2$ are each as defined in item 1', and then the protecting groups still present on the sugar are detached under basic conditions, preferably with sodium hydroxide solution, in order to obtain compounds of the general formula (I) as per item 1'.

7'. The process as claimed in item 6', characterized in that the compound of the general formula (II) to be cyclized is prepared by joining a C2 unit of the general formula (V)

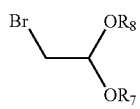
(V)

in which $R_7$ and $R_8$ are each as defined in formula (II) to a protected derivative of L-threose (enantiomerically pure C4 unit) of the general formula (VI)

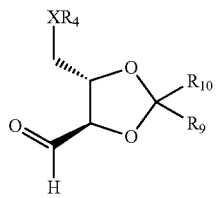
(VI)

in which X, $R_4$, $R_9$, $R_{10}$ are each as defined in formula (II), by known methods, wherein preference is given to C—C bond formation by means of a Grignard reaction in an aprotic solvent such as tetrahydrofuran, and the resulting addition product of the general formula (II) in which [Y=CH—OH] can subsequently be oxidized by known methods such as oxidation with chromium compounds, but preferably by means of Swern oxidation to give the ketone [Y=C(=O)] of the general formula (II), in order then to introduce the nitrogen at position 3 by known methods, for example by reductive amination, but preferably by preparation of an oxime [Y=C(=N)—OH] of the general formula (II), which is subsequently reduced, but, if $R_4$ is hydrogen or a hydroxyl protecting group, may be deprotected beforehand if necessary and derivatized according to the description for $R_4$ in formula (I), in which case the introduction of an unbranched or branched alkyl or heteroalkyl chain on X is effected by known methods, for example Finkelstein reaction, but preferably via a nucleophilic substitution, where the chain to be introduced is activated beforehand with a good leaving groups such as tosylate or mesylate, and then oximes of the general formula (II) [Y=C(=N)—OH] are reduced, for which it is possible to use known methods, preferably a complex hydride in an aprotic solvent such as toluene or THF, forming amines of the general formula (II) [Y=CH—NH$_2$] which are optionally derivatized further or protected at this site [Y=CH—NR$_5$R$_6$] where $R_5$ and $R_6$ are each as defined in the general formula (I).

8'. A compound of the general formula (III)

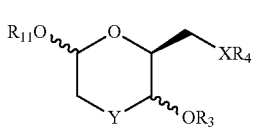
(III)

in which X, Y and $R_4$ are each as defined in formula (II) and $R_6$ and $R_{11}$ are each hydrogen or an activating group known for glycosylation [OC(=O)PhNO$_2$, OTFA] and the wavy lines in each case mean both possible configurations of —OR$_3$ and —OR$_{11}$ in relation to the base structure.

9'. A compound as claimed in item 8', characterized in that $R_3$ and $R_{11}$ are each hydrogen, Y=[CH—NR$_5$R$_6$] where $R_5$ is hydrogen and $R_6$ is TFA, X=O and $R_4$ comprises at least one ethylene glycol unit (—O—CH$_2$—CH$_2$—O—).

10'. A compound as claimed in item 9', characterized in that $R_3$ and $R_{11}$ are each p-nitrobenzoyl.

11'. A compound of the general formula (II)

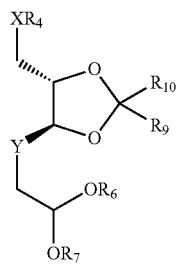

in which $R_7$ and $R_8$ are the same and are each alkyl or alkylene having 2 to 3 carbon atoms; $R_9$ and $R_{10}$ are each an alkyl group having 1 to 3 carbon atoms; X and Y are each as defined in formula (I); $R_4$ is hydrogen or a suitable hydroxyl protecting group as known in the prior art, for instance from "Protective Groups in Organic Synthesis" (Greene, Wuts) 4th edition, John Wiley & Sons, Inc., pages 16 to 288, especially a benzoyl group, or is as defined in formula (I).

12'. The use of compounds of the general formula I alone or in combination with other active ingredients in medicaments.

13'. The use of compounds of the general formula III as a structural element in drugs.

The invention claimed is:

1. A compound of the general formula (IIIa/b)

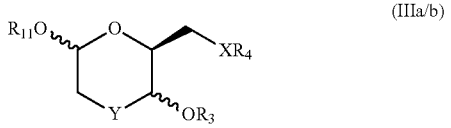

in which $R_3$ and $R_{11}$ are each hydrogen or p-nitrobenzoyl $[C(=O)PhNO_2]$;

$R_4$ is the $(CH_2-CH_2-O)_n-$ group with n=1 to 6, with a hydrogen atom or a $C_1$ to $C_4$ alkyl group bonded to the terminal oxygen atom of the $(CH_2-CH_2-O)_n-$ group;

X=O;

Y=[CH—$NR_5R_6$] in both possible stereoisomeric arrangements, where $R_5$ is hydrogen and $R_6$ is a trifluoroacetyl group (TFA);

and the wavy lines in each case mean both possible configurations of —$OR_3$ or —$OR_{11}$, respectively, in relation to the base structure.

2. A compound having the following formula (Ia):

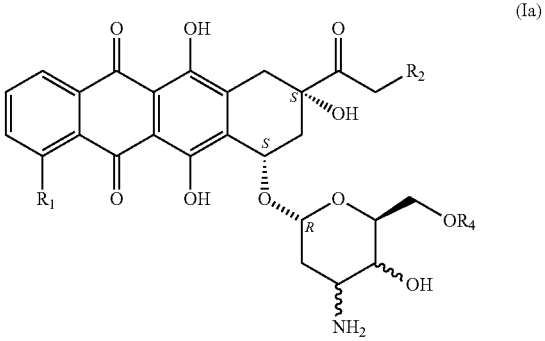

in which $R_1$ is a hydrogen atom or a hydroxyl or methoxy group; $R_2$ is a hydrogen atom or a hydroxyl group; the amino group and also the hydroxyl group may be present in either possible stereochemical arrangement; $R_4$ is the $(CH_2-CH_2-O)_n-$ group with n=1 to 6, with a hydrogen atom or a $C_1$ to $C_4$ alkyl group bonded to the terminal oxygen atom of the $(CH_2-CH_2-O)_n-$ group.

3. A pharmaceutical composition comprising one or more compounds according to claim 2 and optionally one or more pharmaceutically acceptable substances selected from the group consisting of auxiliaries, carriers, diluents and solvents.

4. A pharmaceutical kit comprising (i) one or more compounds according to claim 2, or a pharmaceutical composition as claimed in claim 3, and (ii) at least one antiproliferative or cytotoxic active ingredient.

* * * * *